United States Patent
Crawford

(10) Patent No.: US 8,945,635 B2
(45) Date of Patent: Feb. 3, 2015

(54) FORMULATIONS COMPRISING EXTRACTS FROM PRIMITIVE PLANT SPECIES (MOSSES, FERNS AND LICHENS) TO TREAT AND PREVENT CANCERS

(71) Applicant: Southern Connecticut State University, New Haven, CT (US)

(72) Inventor: Sarah Crawford, Milford, CT (US)

(73) Assignee: Southern Connecticut State University, New Haven, CT (US)

( * ) Notice: Subject to any disclaimer, the term of this patent is extended or adjusted under 35 U.S.C. 154(b) by 0 days.

(21) Appl. No.: 13/964,154

(22) Filed: Aug. 12, 2013

(65) Prior Publication Data

US 2013/0330372 A1    Dec. 12, 2013

Related U.S. Application Data

(62) Division of application No. 12/311,874, filed as application No. PCT/US2007/022149 on Oct. 17, 2007, now Pat. No. 8,507,012.

(60) Provisional application No. 60/852,103, filed on Oct. 17, 2006.

(51) Int. Cl.
*A01N 65/00* (2009.01)
*A61K 45/06* (2006.01)
*A61K 36/09* (2006.01)
*A61K 36/10* (2006.01)
*A61K 36/11* (2006.01)

(52) U.S. Cl.
CPC ................. *A61K 45/06* (2013.01); *A61K 36/09* (2013.01); *A61K 36/10* (2013.01); *A61K 36/11* (2013.01)
USPC ........................................................ 424/725

(58) Field of Classification Search
CPC ........ A61K 36/00; A61K 36/06; A61K 36/18
USPC ................................ 424/725, 195.15, 195.16
See application file for complete search history.

(56) References Cited

FOREIGN PATENT DOCUMENTS

CN              001470252 A  *  1/2004

* cited by examiner

*Primary Examiner* — Michael Meller
(74) *Attorney, Agent, or Firm* — Wood, Herron & Evans, LLP

(57) ABSTRACT

Disclosed are extracts prepared from primitive plants and fungi that have anti-cancer properties. The extracts are prepared by pulverizing the biological matter in a diluent. The extract can be administered to an individual or animal to kill cancer cells, prevent growth of cancer cells and teat cancer. The extracts may be used in combination with other therapeutic protocols.

2 Claims, 28 Drawing Sheets

No Rx                           extract sample 10

Normal colon

Primary cancer (colon)

Metastatic cancer (colon)

(400X) metastatic colon cancer (SW260)

(1000X) primary colon cancer (SW480)

(400X) primary colon cancer (SW480)

(1000X) metastatic colon cancer (SW260)

(400x)

(40x)

Results of treating GBM solid tumor spheroids with carmustine plus curcumin plus extract sample 19 (fern).

227 colon cancer cells, extract sample 13, 14K pellet, 48 hr exposure, 10 mg/mL dose 227 colon primary cancer cells, extract sample 13, 14K supernatant, 48 hr exposure NCI-H1299 lung cancer cells, extract sample 13, filtered 14K pellet, 48 hr exposure NCI-H1299 lung cancer cells, extract sample 13, 14K supernatant, 48 hr exposure GBM cancer cells, extract sample 13, 14K pellet, 48 hr exposure GBM cancer cells, extract sample 13, 14K supernatant, 48 hr exposure GBM cancer cells, extract sample 13, unfiltered 14K pellet, 24 hr exposure, 10 mg/mL dose GBM cancer cells, extract sample 13, 14K supernatant, 24 hr exposure, 10 mg/mL dose 227 primary colon cancer cells, extract sample 13, membrane filtered, 24 hour exposure, 10 mg/mL dose primary colon cancer cells, extract sample 13, unfiltered 14K pellet, 24 hr exposure, 10 mg/mL dose primary colon cancer cells, extract sample 13, 14K supernatant, 24 hr exposure, 10 mg/mL dose primary colon cancer cells, extract sample 13, unfractionated extract, 24 hr exposure, 10 mg/mL dose 227 colon cancer cells, extract sample 13, membrane filtered, 2 day exposure, 10 mg/mL dose 227 primary colon cancer cells, extract sample 13, filtered pellet, 24 hr exposure, 10 mg/mL dose 227 primary colon cancer cells, extract sample 13, 14K supernatant, 24 hr exposure, 10 mg/mL dose 227 primary colon cancer cells, extract sample 13, unfiltered extract, 24 hr exposure, 10 mg/mL dose 227 primary colon cancer cells, untreated control NCI-H1299 cancerous lung cells, untreated control NCI-H1299 cancerous lung cells, extract sample 13, membrane filtered, 24 hr exposure, 10 mg/mL dose NCI-H1299 cancerous lung cells, extract sample 13, pellet (unfiltered), 24 hr exposure, 10 mg/mL dose NCI-H1299 cancerous lung cells, extract sample 13, 14K supernatant, 24 hour exposure, 10 mg/mL dose NCI-H1299 cancerous lung cells, extract sample 13, filtered pellet, 24 hr exposure, 10 mg/mL dose NCI-H1299 cancerous lung cells, extract sample 13, filtered pellet, 2 day exposure, 10 mg/mL dose NCI-H1299 cancerous lung cells, extract sample 13, membrane filtered, 2 day exposure, 10 mg/mL dose NCI-H1299 cancerous lung cells, extract sample 13, 24 hr exposure, 14K supernatant, 10 mg/mL dose NCI-H1299 cancerous lung cells, extract sample 13, 14K supernatant, 2 day exposure, 10 mg/mL dose WI38 normal lung cells, extract sample 13, membrane filtered, 24 hr exposure, 10 mg/mL dose WI38 normal lung cells, extract sample 13, filtered pellet, 2 day exposure, 10 mg/mL dose WI38 normal lung cells, untreated control WI38 normal lung cells, extract sample 13, 24 hr exposure, filtered, 10 mg/mL dose

FORMULATIONS COMPRISING EXTRACTS FROM PRIMITIVE PLANT SPECIES (MOSSES, FERNS AND LICHENS) TO TREAT AND PREVENT CANCERS

CROSS REFERENCE TO RELATED APPLICATIONS

This application is a divisional of U.S. patent application Ser. No. 12/311,874 filed Jan. 29, 2010, which is the U.S. National Phase of International Application No. PCT/US2007/022149 filed Oct. 17, 2007, which claims priority to U.S. Provisional Application No. 60/852,103 filed Oct. 17, 2006, the contents of each of which are incorporated herein by reference in their entirety.

FIELD

The present disclosure relates generally to preparation and use of primitive plant extracts and formulations comprising primitive plant extracts. In one embodiment it is more particularly concerned with formulations comprising primitive plant extracts as a therapeutic agent in combination with at least one other therapeutic agent to kill cancer cells in an individual or animal.

BACKGROUND

Normal body cells grow, divide, and die in an orderly fashion. During the early years of a person's life, normal cells divide more rapidly than needed so that the person will grow until adulthood. After adulthood, cell division in most parts of the body is in balance, with cells dividing to provide only enough new cells to replace worn-out or dying cells and to repair injuries.

Cancer arises from a loss of normal cell division control. In cancerous tissue the cell division balance is disrupted and more new cells than needed to replace worn-out or dying cells are provided. This disruption can result from uncontrolled cell growth or loss of a cell's ability to undergo apoptosis or cell destruction.

The gradual increase in the number of dividing cancer cells creates a growing mass of tissue called a tumor or neoplasm. As more and more of these dividing cells accumulate, the normal organization of the tissue gradually becomes disrupted. Also, during tumor growth the biological behavior of cells slowly changes from the properties of normal cells to cancer-like properties. Some characteristic traits of cancer tumors are an increased number of dividing cells, variation in nuclear size and shape, variation in cell size and shape, loss of specialized cell features, and loss of normal tissue organization.

SUMMARY

Primitive plant samples were processed to form an extract sample. Extract samples from primitive plant species were evaluated with respect to potential anti-cancer properties. Anti-cancer activity of the extract samples included assessment of anti-cancer activity in diverse, unrelated types of human cancer cell lines in vitro, including glioblastoma multiforme (GBM) resistant to conventional chemotherapy; primary colon cancer; metastatic colon cancer; and non-small cell lung cancer. Anti-cancer activity of the extract samples was assessed both in 2-dimensional monolayer cultures and 3-dimensional solid multi-cellular tumor spheroids (MTS) comparable to solid tumor micrometastases in vivo. Anti-cancer activity of the extract samples was assessed based on therapeutic responses in these cancer cells resulting in the induction of cell death. Anti-cancer activity of the extract samples was also assessed with regard to the preventive inhibition of processes associated with solid tumor formation in vitro. Potentially toxic side effects of the extract samples were assessed in normal human cells from tissues similar to the tumor derived cells. Dose/response assays were used to determine optimal therapeutic dosing and linear regression analysis. Formulations comprising one or more extract samples and at least one additional therapeutic agent were evaluated with respect to potential anti-cancer properties.

Briefly, one aspect of the disclosure is the identification of primitive plants having extracts with anti-cancer properties.

Another aspect of the disclosure is the identification of primitive plants from at least one of division bryophyte, division lycopdiophyta, division pterophyta and division ascomycota having extracts with anti-cancer properties.

Another aspect of the disclosure is a method of preparing extracts from primitive plants.

Another aspect of the disclosure is a method of using extracts prepared from primitive plants as a therapeutic agent to kill cancer cells.

Another aspect of the disclosure is a method of using extracts prepared from primitive plants as a therapeutic agent in combination with at least one other therapeutic agent to kill cancer cells.

In general, unless otherwise explicitly stated the disclosed methods, articles and materials may be alternately formulated to comprise, consist of, or consist essentially of, any appropriate steps or components herein disclosed. The disclosed methods, articles and materials may additionally, or alternatively, be formulated so as to be devoid, or substantially free, of any steps, components, materials, ingredients, adjuvants or species used in the prior art or that are otherwise not necessary to the achievement of the function of the present disclosure.

When the word "about" is used herein it is meant that the amount or condition it modifies can vary some beyond that so long as the advantages of the disclosure are realized. The skilled artisan understands that there is seldom time to fully explore the extent of any area and expects that the disclosed results might extend, at least somewhat, beyond one or more of the disclosed limits. Later, having the benefit of this disclosure and understanding the concept and embodiments disclosed herein, a person of ordinary skill can, without inventive effort, explore beyond the disclosed limits and, when embodiments are found to be without any unexpected characteristics, those embodiments are within the meaning of the term about as used herein. It is not difficult for the artisan or others to determine whether such an embodiment is either as expected or, because of either a break in the continuity of results or one or more features that are significantly better than reported in this disclosure, is surprising and thus an unobvious teaching leading to a further advance in the art.

BRIEF DESCRIPTION OF THE DRAWINGS

Referring now to the drawings wherein like elements are numbered alike in the several Figures.

DETAILED DESCRIPTION

Figure 1:
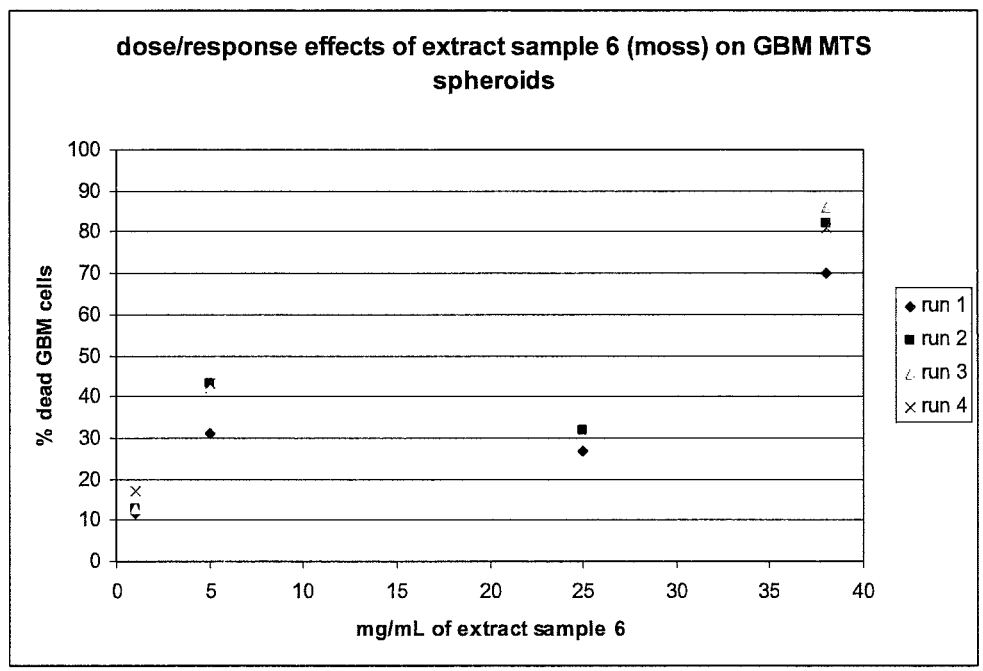
FIG. 1 is a graph of extract sample dose versus cancer cell response.

A better understanding will be obtained from the following detailed description of the presently preferred, albeit illustrative, embodiments of the disclosure.

At least some primitive plants include one or more components that can kill cancer cells. Advantageously, these primitive plants are selected from at least one of division bryophyte, division lycopdiophyta, division pterophyta and division ascomycota.

Primitive plants can be processed to prepare an extract with anti-cancer properties. The extract preparation process advantageously conserves the anti-cancer activity of the plant specimens for use in therapeutic applications.

The extract preparation process comprises isolation of one or more active components present in the primitive plants and optionally purification of the isolated active components. The extract preparation process provides a therapeutic agent comprising an extract sample isolated and optionally purified from one or more primitive plants. While the disclosed extract samples are typically a liquid homogenate containing solid plant particulate matter, the disclosure encompasses an extract sample in any useful form, for example a liquid, a solution, a dispersion or a solid. Isolation can be done by reducing the plant material into small pieces, for example by shredding or chopping or homogenizing. The reducing can be done in the presence of a fluid or the plant pieces can be added to a fluid to prepare an extract.

The extract containing a quantity of the isolated active component can also be purified using well known procedures such as filtration with depth or membrane filtration elements or centrifugation to remove less active fractions or to fractionate homogenate components. The extract can also be purified using well known techniques such as one or more of evaporation, distillation, crystallization or chromatography, singly or in combination, to concentrate and/or isolate the active component or components from a primitive plant extract from other components of the extract. While the disclosed extract is typically liquid, the disclosure encompasses use of primitive plant materials in other forms, for example solids, salts or precursors.

Different types of cells may become cancerous, leading to different types of cancer. A therapeutic agent effective at killing one type of cancer cell may be less effective at killing other types of cancer cells. The primitive plant extract described herein is a therapeutic agent that has pharmacological properties when administered in therapeutically effective amounts for providing a physiological response useful to treat diverse, unrelated types of cancer including glioblastoma multiforme, primary colon cancer, metastatic colon cancer and non-small cell lung cancer.

The active component or components of primitive plant extracts responsible for their anti-cancer properties are believed to be involved in the disruption of cytoskeletal organization in the malignant tumor cells. The biologically active component(s) appear(s) to target cytoskeletal components. The biological targeting of the actin cytoskeleton by primitive plant extracts is significant in that the disruption of the cytoskeletal network may directly initiate cell death responses. Previous studies in the Cancer Biology Laboratory at Southern Connecticut State University (New Haven, Conn.) have determined that solid tumor formation requires functional focal adhesion kinase and that therapeutic agents that target this enzyme cause tumor cell death. Thus, there appears to be a direct connection between cytoskeletal disruption by a primitive plant extract and the induction of cell death in malignant tumors.

The broad spectrum anti-tumor responses elicited by biologically active primitive plant extracts implicates the cytoskeletal network structure/adhesion complexes as a primary therapeutic and preventive target common to many human cancers. Moreover, the significance of the cytoskeleton as a biological therapeutic and also a preventive target of primitive plant extracts implicates a broad spectrum of cell pathways and regulatory cycles that may be affected by primitive plant extract activity.

As used herein a "therapeutically effective amount" of a formulation is the quantity of that formulation which, when administered to an individual or animal, results in a sufficiently high level of that formulation in the individual or animal to cause a physiological response, for example a discernible decrease in a cancer cell population. The specific dosage level of formulation will depend upon a number of factors, including, for example, dosage of each active component in the formulation, biological activity of the particular extract, exposure time of the cancer cell to the formulation, age, body weight, sex and general health of the individual or animal being treated. Typically, a "therapeutically effective amount" of a primitive plant extract sample is believed to range from about 1 mg/mL to about 100 mg/mL and advantageously from about 5 mg/ml to about 50 mg/ml. Typically, a "therapeutically effective amount" of a formulation comprising an extract as a therapeutic agent and at least one other therapeutic agent is believed to range from about 1 mg/mL to about 1,000 mg/mL. As used herein, an "individual" refers to a human. An "animal" refers to, for example, veterinary animals, such as dogs, cats, horses and the like, and farm animals, such as cows, pigs and the like.

The disclosed extract can be administered by a variety of known methods, including orally, rectally, or by parenteral routes (e.g., intramuscular, intravenous, subcutaneous, nasal or topical). The form in which the extract is administered will be determined by the route of administration. Such forms include, but are not limited to, capsular and tablet formulations (for oral and rectal administration), liquid formulations (for oral, intravenous, intramuscular, subcutaneous, ocular, intranasal, inhalation-based and transdermal administration) and slow releasing microcarriers (for rectal, intramuscular or intravenous administration). The formulations can also comprise one or more of a physiologically acceptable excipient, vehicle and optional adjuvants, flavorings, colorants and preservatives. Suitable physiologically acceptable vehicles include, for example, saline, sterile water, Ringer's solution and isotonic sodium chloride solutions.

The following examples are included for purposes of illustration so that the disclosure may be more readily understood and are in no way intended to limit the scope of the disclosure unless otherwise specifically indicated.

Test Methods and Protocols

Initiating Cell Lines

All cell lines used in the examples were obtained from the American Type Culture Collection, Manassass, Va. US (ATCC). The cell lines tested include a plurality of human malignant lines including DBTRG-GBM glioblastoma multiform (GBM, ATCC No. crl-2020); SW620 metastatic colon cancer (ATCC No. ccl-227); SW480 primary colon cancer (ATCC No. ccl-228); and NCI-H1299 non-small cell lung cancer. Typically, the cell lines were maintained in standard culture media (RPMI 1640 from Gibco supplemented with 10% fetal bovine serum (FBS) and 1% sodium pyruvate from Gibco). Cell lines were cultured as monolayers for routine passage and subculture and were also cultured in the form of three dimensional multicellular tumor spheroids (MTS) on dishes coated with 1% agarose as an attachment inhibitor for treatment assays. The following procedure was followed after the cells were received or when new cell lines which were previously frozen needed to be started up. When the cells came from the ATCC, they were stored in dry ice. When the cells were frozen down, they were stored in liquid nitrogen.

Two (1.5 mL) vials were obtained and the cell line and date were written on each vial.

Six milliliters of the appropriate media (appropriate for the cell line) was added to each vial.

All but the cap portion of each vial was submerged in a 37° C. bath until the cells are thawed.

The cells are inoculated into flasks and the flasks were then placed horizontally in the incubator (37° C., 10% $CO_2$) and checked daily.

Cell Passaging—Maintenance of Monolayer Cell Cultures.

The various cell lines were tested using flasks containing confluent cells. The contents of the flasks were divided into multiple flasks or culture dishes in order to prevent cell death due to overpopulation and to create a greater quantity of cells to analyze. The ratio of vials of confluent cells to vials containing fresh medium was dependent on how aggressive the cell line was.

Cell Passaging—Prior to Working with the Cells:

The vials of cells to be passaged as well as the bottles of trypsin, PBS and the appropriate medium (per ATCC: RPMI 1640 for GBM and NCI-H1299 cell lines, Leibovitz 015 for colon cell lines) were obtained. The outside of each container was cleaned.

Two sterile culture flasks were obtained and the cell line and date were written on each.

5 mL of fresh appropriate medium was added to each vial.

Cell Passaging—Working with the Cells:

The flasks containing desired cells were taken out of the incubator and observed under a light microscope to make sure the cells were visibly healthy, unstressed and not contaminated.

The medium that was in the flasks was extracted using a Pasteur pipette and discarded.

1 mL of Phosphate Buffer Solution (PBS) was then added to each flask and was allowed to sit on the cells for 2 minutes.

The PBS was then pipetted up and down, removed, and discarded.

1 mL of trypsin was then added to each of the flasks, allowed to sit for 1-2 minutes and pipetted up and down vigorously until the cells were detached from the substrate and floating.

1 mL of appropriate medium was then added to each of the cell containing flasks and mixed well via pipetting.

The desired quantity of cells was placed in empty flasks or dishes containing fresh medium, caps were placed on the flasks (tight or loosely depending on the amount of $CO_2$ necessary) and the flasks were placed into the incubator.

Laminin Substrate Formation:

40 µl of laminin (10 g/mL in solution—Available from Sigma-Aldrich, St. Louis Mo.) was thawed and vortexed.

A sterile 15 ml tube was then obtained, and 10 ml of PBS was added.

The laminin solution was then added to the 15 ml tube and inverted several times to mix.

0.5 ml portions of the solution were then added to 1 cm dishes.

The 24 well dish was then placed into the incubator at 37° C. for 2 to 12 hours.

The liquid laminin was then gently removed from each of the wells.

0.5 ml of media was then added to each of the wells.

Freezing Down Cells

Because there are many ways in which cell lines could be contaminated or otherwise ruined, once a stock has been successfully initiated, some of the cells are frozen down to ensure that an entire cell line is not lost. After this process, the cells are in the same state as when they came from the ATCC.

Prior to Working with the Cells:

The flasks of the cells to be passaged as well as the bottles of trypsin, PBS, and the appropriate medium were obtained, and the outside of the containers were cleaned.

The appropriate number of sterile 2 mL nunc tubes with screwcaps were obtained and the cell line and date were written on each.

About 0.1 mL of dimethyl sulfoxide (DMSO) used as a cryopreservant is added to each of the 2 mL tubes to produce a final concentration in the medium and cells of 10%.

For Cell Lines which Adhere to the Substrate:

The flasks containing the cells were taken out of the incubator, and observed under a light microscope to make sure that the cells are visibly healthy, unstressed and not contaminated.

The medium that was in the flasks was extracted using a Pasteur pipette, and transferred to the waste container.

1 mL of PBS was then added to each of the flasks, and was allowed to sit on the cells for 2 minutes.

The PBS was then pipetted up and down, removed, and discarded.

0.5 mL of trypsin was then added to each of the flasks, allowed to sit for 1-2 minutes, and pipetted up and down vigorously until the cells were detached from the substrate and floating.

0.5 mL of the appropriate medium was then added to each of the vials and mixed well with the cells via pipetting.

A sterile test tube is obtained and labeled appropriately.

The cap of the appropriately labeled tube was carefully unscrewed, and 1 mL of the cell/medium mixture is added. The cap is replaced and this process is continued until all of the mixture was utilized.

The 2 mL tubes are placed in an isopropanol bath and the bath and tubes are placed into a freezer to cool them in a consistent manner at approximately 1° C./minute.

After cooling the cells are placed in liquid nitrogen for long term storage.

Solid Tumor Spheroid Culture Conditions—Preparing the Plates:

1% Argarose gel was poured into each well of a 24 well dish.

The plates were then kept flat and allowed to cool for a few minutes.

Plates were sealed and stored at 4 C.

Preclinical Treatment Protocols

Preclinical assessment of the effects of experimental therapeutics on solid tumor spheroid formation involved simultaneous plating of tumor cells on agarose with addition of therapeutic agent. If the cells were being treated to see if solid tumors would be destroyed by the treatment, then the therapeutic agent was added after the tumors were well established (after at least 24 hours).

Preparing and Treating the Cells—

For monolayer cultures that adhere to the substrate:

The medium in the flask is extracted using a Pasteur pipette and discarded.

1 mL of PBS is added to each flask and is allowed to sit on the cells for 2 minutes.

The PBS is then pipetted up and down, removed and discarded.

1 mL of trypsin is then added to each flask, allowed to sit for 1-2 minutes and pipetted up and down vigorously until the cells were detached from the substrate and floating.

1 mL of the appropriate medium is then added to each of the flasks and mixed well via pipetting.

The cells are then divided evenly amongst the wells containing the agarose. This was usually done in a 1:6 ratio (1 vial of cells to 6 wells).

Dose Response Assays

Dose response assays were done in order to determine the optimum dose range for experimental therapeutics. Typically, extracts prepared from 50 mg plant material/mL media; 37.5 mg plant material/mL media; 25 mg plant material/mL media; 12.5 mg plant material/mL media; and 5 mg plant material/mL media were used. The dose response assay typically followed the following protocol.

A sterile 24 well, 1 cm dish is obtained and the amount of medium and extract, the cell line used, as well as the date were labeled. Cell cultures were initiated at least 24 hours prior to treatment and were assessed at levels of cell density confluence between 50 to 75%.

The appropriate amount of medium and therapeutic agent is added to each well.

The cells are either detached from the substrate or spun down depending on the cell line.

The cells are then pipetted evenly into the wells in a 1:6 ratio (contents of 1 vial per 6 wells) at an approximate plating density of $1 \times 10^5$ cells per 1 $cm^2$ culture well. The 24 well dish is placed in the incubator at 37° C.

At the desired time a predetermined amount of therapeutic agent is added to each well.

The 24 well dish is placed in the incubator at 37° C.

After the desired treatment interval (typically ranging from hours to several days) viability assays are conducted to assess the effects of each therapeutic agent on each cell line examined.

The 24 well dish containing treated (and control) samples was taken out of the incubator and placed in the hood.

The cells in each well are observed under a light microscope and photographs taken.

Cytotoxic effects of the experimental treatments were assessed by the trypan blue exclusion method.

Trypan Blue Exclusion Method

The method includes Part A dependent on the cell culture followed by a common Part B.

Part A—for Cells which Adhere to the Substrate:

A sterile micro centrifuge tube is obtained and labeled appropriately.

The medium from each well is taken off and placed into the appropriately labeled micro centrifuge tube using separate Pasteur pipettes for each well sample.

6 drops of PBS is added to each well.

Two minutes later, the PBS is taken off of each well and placed into the appropriate tubes (using separate pipettes).

6 drops of trypsin is added to each well.

Two minutes later, the cells in each well are pipetted up and down vigorously (using separate pipettes) until all of the cells are off of the substrate.

The cell mixture from each well is pipetted into the appropriate tube.

Part A—For Non-Adherent Solid Tumor Spheroid Cultures:

A sterile micro centrifuge tube is obtained and labeled appropriately.

The medium from each of the wells is taken off and placed into the appropriately labeled tube.

Part B—For all of the Cell Lines:

The caps were then tightened on each of the micro centrifuge tubes. The micro centrifuge tubes are placed evenly in a micro centrifuge and centrifuged at 10,000 RPM for 10 minutes.

The tubes are checked to make sure that tight pellets are formed.

The supernatant is removed from each of the tubes (using separate pipettes) making sure to keep the pellet in the tube. If the pellet falls apart, the micro centrifuge tube is respun and this process was repeated.

100 μL of PBS is added to each of the tubes and pipetted vigorously until the pellet is completely dissolved into the smallest pieces possible.

100 μL of trypan blue is added to the tube and pipetted vigorously.

The cells are incubated in trypan blue stain for about fifteen to thirty minutes before cell counts are commenced.

A clean slipcover is placed onto a hemacytometer.

The sample is pipetted onto the hemacytometer and placed under a light microscope for viable cell counts.

The plasma membrane of live (viable) cells excludes the trypan blue stain so that these cells appear clear under microscopic observation. Conversely, the plasma membrane of dead or dying cells becomes more porous and permeable to the trypan blue stain. Dying and dead cells will appear blue under microscopic observation. While the trypan blue stain does not definitively ascertain cell health, it does allow a very good estimation of the number of total cells, dead cells and live cells in a culture.

Plant Collection

The plant specimens were collected from their native habitats, located in moist areas throughout southwestern Connecticut. Although the first samples were collected in and around bogs, there did not appear to be a dramatic difference between the overall effectiveness of those plants and the ones collected from higher elevations. Patches of the plants were found, but only small samples were taken from each of the patches. A great deal of effort was taken to avoid disturbing the environment both when hiking and collecting samples. After the specimen was collected, it was placed in a zip lock freezer bag. When there was a lengthy duration between the time the sample was harvested and the time in which it would be processed into an extract, a small amount of water was added to the sample in order to keep it moist.

Plant Storage

One suitable method for storing the collected samples is placing the sample in a plastic bag with a small a mount of water followed by sealing the bag. Exposure of the bagged samples to light created a moist environment found suitable for sample storage.

Plant Extract Preparation Procedure

Plant Matter to Media Ratios

Small quantities of fresh samples were collected from the surrounding area. One portion of that sample was utilized to create an extract and another portion of the sample was allowed to grow in the terrarium for future use. Some portions were also frozen.

The following procedure was found to be effective. The plant sample is first dried using clean paper towels. The sample is squeezed several times until it is completely dry. The sample is weighed. Typically, a 4 g sample would yield enough plant matter to obtain at least 2.5 g of cleaned material. It was found that 2.5 g of the aforementioned plants worked well when ground into 25 mL of media (90% RPMI 1640, 10% FBS).

Plant Cleansing Process

For each sample, 6 sterile 50 mL plastic centrifuge tubes (stored under UV light to maintain sterility before use) were obtained.

Each tube was labeled according to the sample that it would contain, and which step of the process (1-6) it was.

The first tube contained 20 mL of ETOH.

Tubes 2-5 each contained 20 mL of deionized water which had been autoclaved and stored under UV light to maintain sterility.

Tube 6 contained a quantity of media (90% RPM 10% FBS).

The appropriate plant material was then placed into tube 1 using sterile tweezers.

The tube was then inverted several times over the course of a minute.

The plant material was then placed in paper towels (stored under UV light to maintain sterility) until the EtOH was removed.

The EtOH rinsed plant material was transferred using sterile tweezers to tube 2 and inverted several times over the course of a minute.

The plant material was then transferred using sterile tweezers to tubes 3, 4, and 5 after inverting each of them several times over the course of a minute.

The cleaned plant material was then dried using paper towels.

The clean, dry, plant material was then weighed again (approximately 2.50 g). Plant material in excess of the 2.5 gm amount could be used to create additional extracts if desired.

The Homogenization Process

The appropriate quantity of plant material (typically 2.50 g) and the appropriate quantity of media (typically 25 mL) was then placed in the inverted cup component of a Pro Chopper (mini blender). This provides a homogenate of about 100 mg plant material/1 mL of media. As used herein with respect to extract samples reference to mg/mL means the extract sample was prepared from, or diluted to, the recited number of mg of plant material/the recited number of mL of diluent, e.g. a weight to volume type ratio.

The bottom portion containing the blades was then attached.

The whole structure was then inverted and placed on the piece containing the motor (the bottom piece of a blender).

The plant material was ground for 30 seconds, swirled, and ground for another minute.

The homogenized solution (extract) was then poured into a 50 mL centrifuge tube.

Typically, the extract pH was about 7.0 to 7.4. The homogenate may be diluted prior to use if desired. Extract concentrations used in tumor assessments ranged from about 5 mg plant material/mL media to about 50 mg plant material/mL of media Cleaning the Chopping Device The device was cleaned using Alconox, warm water and a glassware cleaning brush. A small amount of ETOH was then utilized to rinse the device. The device was then rinsed with deionized water, dried thoroughly, and placed under UV light until the next extract was ready to be homogenized.

Extract Storage

Several forms of storage were tested, including storing the extract in the 50 mL plastic tubes, spinning down the extracts and then storing the liquid portion in the 50 mL tubes, as well as many others. The most practical forms of storage is:

Plant extracts are stored in a refrigerator overnight to maximize solubilization of plant materials prior to use.

Extracts are spun down in 50 mL tubes in a refrigerated centrifuge for 45 minutes at a low speed to remove large particulate matter (20 minutes at 5,000 RPM, and 25 minutes at 5,500 RPM). The solid portion is discarded and the liquid portion is then spun down in a micro centrifuge at 10,000 RPM for 10 minutes. The centrifuged extracts included liquid and any solid. The extract could be used or stored in a refrigerator at 4° C. Some extracts were stored in a freezer with no loss of efficacy.

Confocal Staining and Imaging

Prior to testing 12 well dishes were set up:

Because the higher magnifications could not be utilized when the cells were in the dishes as the confocal microscope did not have an inverted lens setup, the cells were plated with slipcovers in the dishes which could be removed.

Small plastic slip covers were cut to size (small enough to fit in the wells) using scissors and placed in a 12 1.5 $cm^2$ well dish.

EtOH was then added to each of the wells to ensure that they remained sterile.

The EtOH was then added to each of the wells to ensure that they remained sterile.

The EtOH was then removed from the wells (when ready to use) and each well was washed two times using PBS.

1 mL of media was then added to each of the 12 wells.

Cells from flasks in the incubator were then detached from the substrate: the media was removed, 1 mL of PBS was added, the solution was pipetted, and the PBS was removed. 1 mL of trypsin was then added, pipetted, and removed, 1 mL of media was then added and pipetted as well. The cells were then distributed to the prepared culture wells at a plating density of about $1 \times 10^5$ cells per well.

1.5 mL samples of the previously prepared extracts were then placed into labeled 2.0 mL tubes and spun in the micro centrifuge for 10 minutes at 10,000 RPM to pellet particulate plant material immediately prior to use.

0.5 mL samples of each of the extracts were then added to the appropriate well with the slipcover to achieve a final concentration of 50 mg/mL per cell culture assay.

The samples were then incubated at 37° C. until the following day.

Day Two: Cell Fixation and Staining for Confocal Laser Imaging.

Method for Staining Using Tetramethyl Rhodamine Beta Isothiocyanate Phalloidain.

The media was extracted and disposed of.

PBS was then added and removed to wash the cells.

The cells were then rinsed with 10% neutral buffered formalin for 15 minutes at room temperature to fix them.

(While still in the formalin) the cells were placed at 4° C. (in the refrigerator) for an additional 15 minutes.

The formalin was then taken off and discarded.

PBS was then utilized to rinse the cells and disposed of.

A 10% triton-X100 (detergent) solution was then utilized to permeabilize the cells. The triton solution was then added to the cells and the cells were allowed to remain in the solution for 5 minutes.

The triton-X100 solution was removed with a pipette.

The cells were then rinsed with PBS 2 times. The second time the cells were stored in PBS until the phalloidin was ready.

Tetramethyl rhodamine beta isothiocyanate phalloidin (available from Sigma-Aldrich, St. Louis, Mo.) was then diluted (5 mg/L) in a 1:1000 dilution in PBS.

Samples of the phalloidin mixture were then placed in each of the wells (in the dark and were then allowed to sit in the dark for 20 minutes.

The cells were then rinsed again with PBS

The slip covers were then taken out of the wells and placed onto labeled slides using sterile tweezers.

The cells were then viewed (and pictures were taken) using the confocal laser microscope (set at 500 nm excitation wavelength). The tetramethyl rhodamine beta isothiocyanate phalloidin makes actin fluoresce green.

Some of the cells were very hard to find, especially in wells having many dead cells because they were so sparse. Lower magnification can be utilized in order to find the cells before higher magnifications is utilized. Typically, photomicroscopy imaging was performed at total magnifications of 100× to 1,000×.

EXAMPLES

The following examples are included for purposes of illustration so that the disclosure may be more readily understood and are in no way intended to limit the scope of the disclosure unless otherwise specifically indicated.

The plant materials used include:

```
Kingdom Plantae
    Division Bryophyta
        Class Bryopsida - true mosses
Kingdom Plantae
    Division Bryophyta
        Class Sphagnopsida - peat mosses
Kingdom Plantae
    Division Lycopdiophyta
        Class Lycopodiopsida
            Order Lycopodiales
                Family Lycopodiaceae - club mosses
Kingdom Plantae
    Division Pterophyta
        Class Filicopsida
            Order Polypodiales
                Family Thelypteridaceae - marsh ferns
Kingdom Plantae
    Division Pterophyta
        Class Filicopsida
            Order Polypodiales
                Family Dryoptereridaceae - wood ferns
Kingdom Fungi
    Division Ascomycota
        Class Lecanoromycetes
            Order Lecanorales
                Family Physciaceae - including Physcia grisea
```

Extracts were made from the following specimens. Unless otherwise indicated each listed extract sample was prepared from a different plant specimen.

TABLE 1

| extract sample | plant specimen used in extract sample |
|---|---|
| 1 | sphagnum moss |
| 2 | sphagnum moss |
| 3 | sphagnum moss |
| 4 | sphagnum moss |
| 5 | sphagnum moss |
| 6 | sphagnum moss |
| 7 | maidenhair fern |
| 8 | tree fern |
| 9 | club moss |
| 10 | club moss |
| 11 | club moss |
| 12 | club moss |
| 13 | Christmas fern |
| 14 | lichen |
| 15 | sphagnum moss |
| 17 | club moss |
| 18 | club moss |
| 19 | Christmas fern. This is a second extract made using the plant material of sample 13. |
| 20 | tree fern |
| 21 | lichen |
| 22 | club moss |

Dose/Response Effects of Extract Samples

Dose/response effects of 3 day exposure of extract sample 6 (moss) on glioblastoma multiforme cells.

The dose response assay was done as previously disclosed. Extract sample 6 (moss) was applied to glioblastoma multiforme multi-cellular tumor spheroid (MTS) culture and incubated for 3 days at 37° C.

TABLE 2 dose/response effect, 3 day exposure, GBM MTS cells

| dose | % dead cells, run 1 | % dead cells, run 2 | % dead cells, run 3 | % dead cells, run 4 |
|---|---|---|---|---|
| 1 mg/mL | 12 | 13 | 13 | 17 |
| 5 mg/mL | 31 | 43 | 42 | 43 |
| 25 mg/mL | 27 | 32 | — | — |
| 38 mg/mL | 70 | 82 | 86 | 81 |

The results are graphically shown in FIG. 1.

Dose/response effects of 3 day exposure of extract sample 14 (lichen) on glioblastoma multiforme three dimensional multi-cellular tumor spheroids (MTS) cells.

The dose response assay was done as previously disclosed. Extract sample 14 (lichen) was applied to glioblastoma multiforme three dimensional multi-cellular tumor spheroids (MTS) and incubated for 3 days at 37° C.

TABLE 3 dose/response effect, 3 day exposure, GBM MTS cells

| dose | % dead cells, run 1 | % dead cells, run 2 | % dead cells, run 3 | % dead cells, run 4 |
|---|---|---|---|---|
| 0 mg/mL | 6 | 8 | 13 | 9 |
| 5 mg/mL | 23 | 22 | 24 | 20 |
| 12.5 mg/mL | 21 | 14 | — | — |
| 25 mg/mL | 35 | 26 | 29 | 32 |
| 38 mg/mL | 50 | 50 | — | — |
| 50 mg/mL | 54 | 64 | 56 | 74 |

Figure 2:
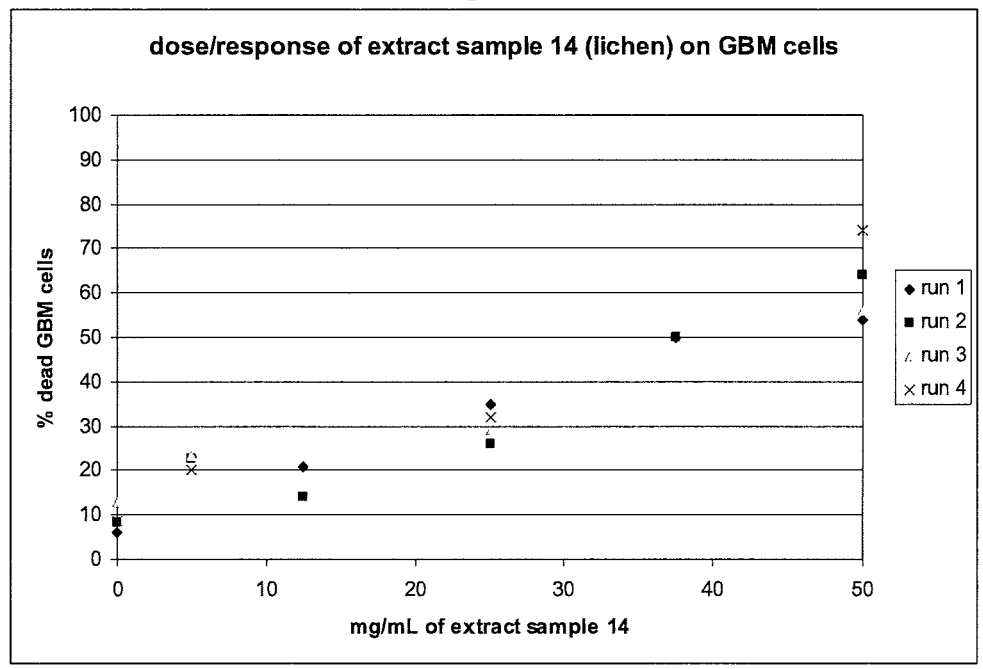
FIG. 2 is a graph of extract sample dose versus cancer cell response.

The results are graphically shown in FIG. 2.

Dose/response effects of 3 day exposure of extract sample 12 (club moss) on glioblastoma multiforme three dimensional multi-cellular tumor spheroids (MTS) cells.

The dose response assay was done as previously disclosed. Extract sample 12 (moss) was applied to glioblastoma multiforme three dimensional multi-cellular tumor spheroids (MTS) and incubated for 3 days at 37° C.

TABLE 4 dose/response effect, 3 day exposure, GBM MTS cells

| dose | % dead cells, run 1 | % dead cells, run 2 | % dead cells, run 3 | % dead cells, run 4 |
|---|---|---|---|---|
| 12.5 mg/mL | 32 | 45 | 26 | 63 |
| 25 mg/mL | 55 | — | — | — |
| 38 mg/mL | 86 | 55 | 83 | 74 |

Figure 3:
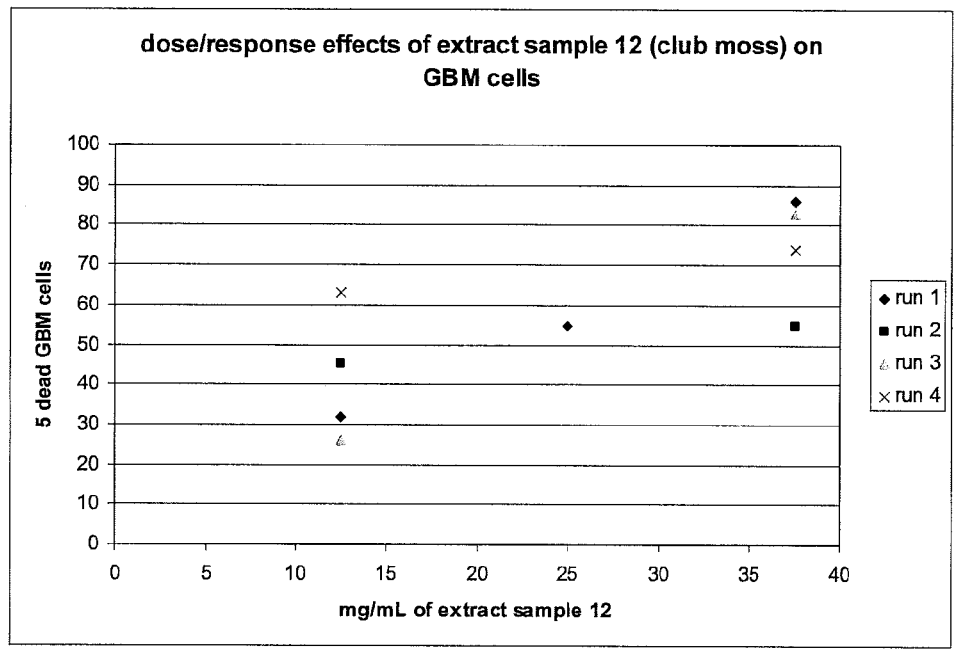
FIG. 3 is a graph of extract sample dose versus cancer cell response.

The results are graphically shown in FIG. 3.

Dose/response effects of 3 day exposure of extract samples 10 (moss), 11 (moss) and 13 (fern) on glioblastoma multiforme three dimensional multi-cellular tumor spheroids (MTS) cells.

The dose response assay was done as previously disclosed. Extract samples were applied to glioblastoma multiforme three dimensional multi-cellular tumor spheroids (MTS) and incubated for 3 days at 37° C.

TABLE 5 dose/response effect, 3 day exposure, GBM cells

| dose | % dead cells control | % dead cells 10 | % dead cells 11 | % dead cells 13 |
|---|---|---|---|---|
| 25 mg/mL | 12 | 17 | 27 | 34 |
| 50 mg/mL | — | 23 | 17 | 24 |

Figure 4:
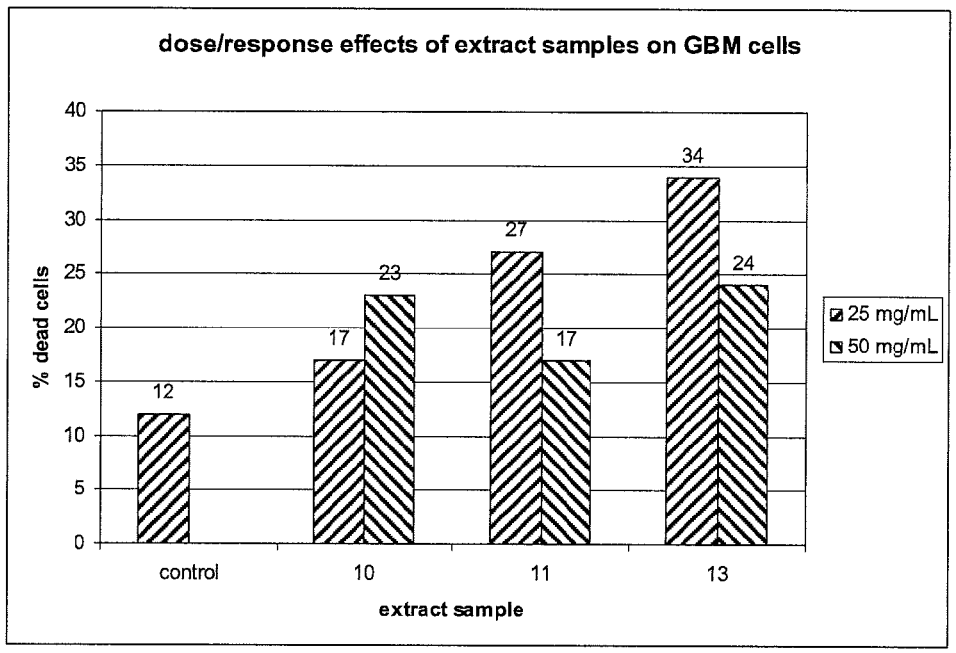
FIG. 4 is a graph of extract sample dose versus cancer cell response.

The results are graphically shown in FIG. 4.

Glioblastoma Multiforme (Monolayer Culture) Cell Death after Three Day Exposure to 50 mg/mL Extracts from Sphagnum Moss.

Samples of GBM cells in a monolayer culture were exposed to single extract samples and incubated for three days. After incubation the sample was split with one portion being stained with trypan blue and microscopically assessed and a second portion being replated for a recovery assay.

TABLE 6

GBM cell death, 3 day exposure, 50 mg/mL extract samples

| extract sample | Total | Blue | Viable | % Dead | Ave. % Dead | Ave. % Dead by species |
|---|---|---|---|---|---|---|
| control 1 | 47 | 3 | 44 | 0.063 | | |
| | 42 | 2 | 40 | 0.047 | | |
| | 36 | 6 | 30 | 0.167 | | |
| | 34 | 7 | 27 | 0.206 | 0.121 | |
| control 2 | 21 | 7 | 14 | 0.333 | | |
| | 36 | 15 | 21 | 0.420 | | |
| | 35 | 7 | 28 | 0.200 | | |
| | 32 | 6 | 4 | 0.188 | 0.285 | |
| control 1 & 2 average | | | | | | 0.203 |
| 1, sphagnum moss, run 1 | 32 | 10 | 22 | 0.313 | | |
| | 31 | 15 | 16 | 0.483 | | |
| | 35 | 15 | 20 | 0.429 | | |
| | 39 | 12 | 27 | 0.307 | 0.383 | |
| 1, sphagnum moss, run 2 | 35 | 14 | 21 | 0.400 | | |
| | 33 | 12 | 21 | 0.364 | | |
| | 30 | 9 | 21 | 0.300 | | |
| | 33 | 11 | 22 | 0.333 | 0.349 | |
| 1, sphagnum moss ave. | | | | | | 0.366 |

TABLE 6-continued

GBM cell death, 3 day exposure, 50 mg/mL extract samples

| extract sample | Total | Blue | Viable | % Dead | Ave. % Dead | Ave. % Dead by species |
|---|---|---|---|---|---|---|
| 2, sphagnum moss, run 1 | 48 | 23 | 26 | 0.479 | | |
| | 77 | 28 | 49 | 0.364 | | |
| | 78 | 27 | 51 | 0.346 | | |
| | 73 | 30 | 43 | 0.411 | 0.400 | |
| 2, sphagnum moss, run 2 | 40 | 17 | 33 | 0.425 | | |
| | 59 | 18 | 41 | 0.305 | | |
| | 55 | 22 | 33 | 0.400 | | |
| | 57 | 23 | 34 | 0.404 | 0.383 | |
| 2, sphagnum moss ave. | | | | | | 0.392 |
| 3, sphagnum moss, run 1 | 34 | 9 | 25 | 0.265 | | |
| | 23 | 11 | 12 | 0.478 | | |
| | 23 | 11 | 12 | 0.478 | | |
| | 23 | 8 | 15 | 0.348 | 0.392 | |
| 3, sphagnum moss, run 2 | 96 | 31 | 65 | 0.323 | | |
| | 91 | 31 | 70 | 0.341 | | |
| | 67 | 22 | 45 | 0.328 | | |
| | 99 | 36 | 63 | 0.363 | 0.339 | |
| 3, sphagnum moss, ave. | | | | | | 0.366 |

Figure 5:
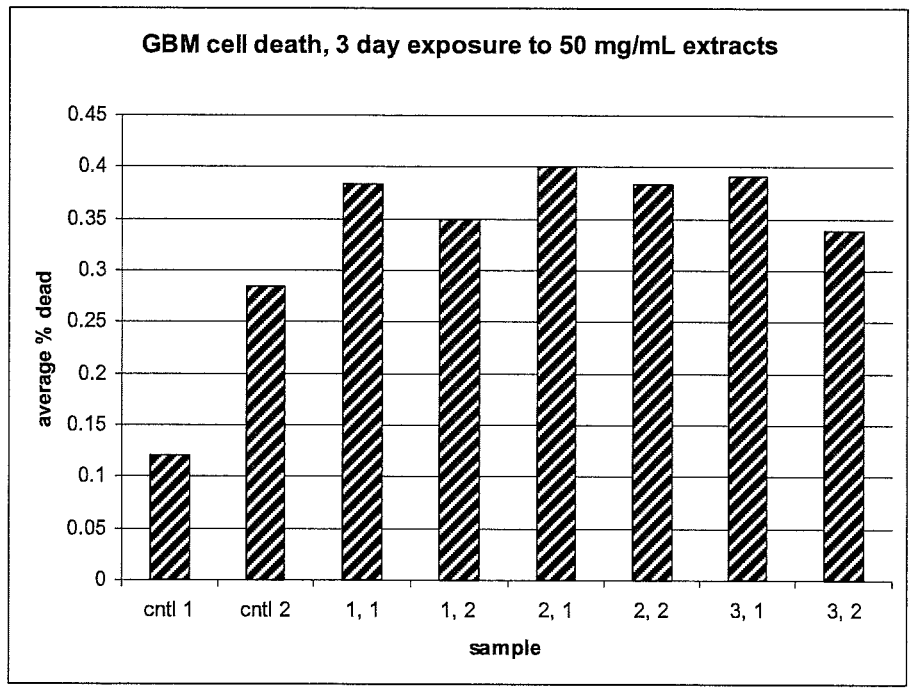
FIG. 5 is a graph of GBM cancer cell death after exposure to extract samples.

The results are graphically shown in FIG. 5.

Recovery Assay: Glioblastoma Multiforme Cell Death after 3 Day Exposure to 50 mg/mL Extracts from Sphagnum Moss; Replating and Recovery for 3 and 5 Days The split cell samples from Table 6 were replated and incubated for 3 and 5 days. After incubation the replated cells were assayed for recovery.

TABLE 7

Recovery assay, GBM cell death, 3 day recovery

| extract sample | Total | Dead | Alive | % Dead | Ave. % Dead |
|---|---|---|---|---|---|
| control | 13 | 3 | 10 | 0.231 | |
| | 23 | 5 | 18 | 0.217 | |
| | 20 | 4 | 16 | 0.200 | |
| | 19 | 5 | 15 | 0.263 | 0.228 |
| 2, sphagnum moss | 26 | 11 | 15 | 0.423 | |
| | 16 | 7 | 9 | 0.438 | |
| | 18 | 9 | 9 | 0.500 | |
| | 25 | 15 | 10 | 0.600 | 0.490 |
| 3, sphagnum moss | 37 | 18 | 18 | 0.486 | |
| | 45 | 23 | 22 | 0.511 | |
| | 37 | 27 | 30 | 0.729 | |
| | 66 | 26 | 40 | 0.394 | 0.530 |

TABLE 8

GBM cell death, 5 day recovery

| Sample | Total | Dead | Alive | % Dead | Ave. % Dead |
|---|---|---|---|---|---|
| control | 20 | 4 | 16 | 0.200 | |
| | 18 | 5 | 13 | 0.278 | |
| | 23 | 5 | 18 | 0.217 | |
| | 24 | 6 | 18 | 0.250 | 0.236 |
| 1, sphagnum moss | 14 | 6 | 8 | 0.429 | |
| | 21 | 7 | 14 | 0.333 | |
| | 18 | 9 | 9 | 0.500 | |
| | 15 | 6 | 9 | 0.400 | 0.416 |
| 2, sphagnum moss | 22 | 7 | 19 | 0.318 | |
| | 25 | 9 | 16 | 0.360 | |
| | 29 | 10 | 19 | 0.349 | |
| | 26 | 10 | 16 | 0.384 | 0.352 |

TABLE 8-continued

GBM cell death, 5 day recovery

| Sample | Total | Dead | Alive | % Dead | Ave. % Dead |
|---|---|---|---|---|---|
| 3, sphagnum moss | 14 | 5 | 9 | 0.357 | |
| | 16 | 7 | 9 | 0.438 | |
| | 18 | 8 | 10 | 0.444 | |
| | 16 | 7 | 9 | 0.438 | 0.419 |

The average results for the above Tables are summarized below.

| extract sample | average % dead cells after 3 day exposure | average % dead cells after 3 day recovery | average % dead cells after 5 day recovery |
|---|---|---|---|
| control | 20.3 | 22.8 | 23.6 |
| 1, sphagnum moss | 36.6 | — | 41.6 |
| 2, sphagnum moss | 39.2 | 49.0 | 35.2 |
| 3, sphagnum moss | 36.6 | 53.0 | 41.9 |

Figure 6:
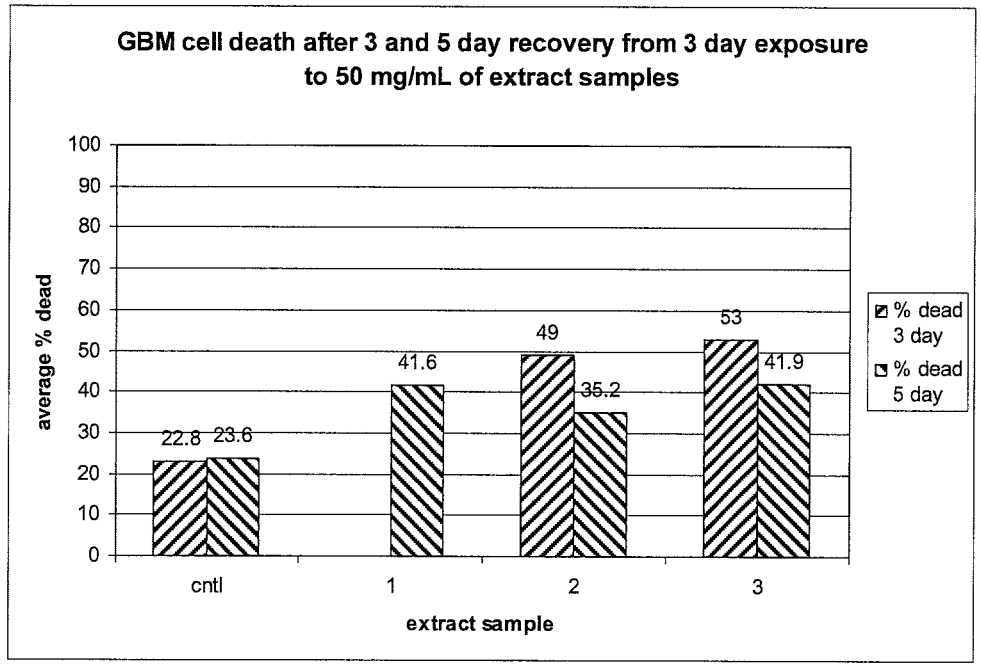
FIG. 6 is a graph of GBM cancer cell recovery after exposure to extract samples.

FIG. 6 graphically illustrates the average glioblastoma multiforme cell death after the three and five day recoveries.
Glioblastoma Multiforme Cell Death after Exposure to 50 mg/mL Extracts from Moss or Fern for Two Days.

TABLE 9

GBM cell death, 2 day exposure

| extract sample | Total | Dead | Alive | % Dead | Ave. % Dead |
|---|---|---|---|---|---|
| control | 161 | 12 | 149 | 0.075 | |
| | 147 | 21 | 126 | 0.143 | |
| | 150 | 18 | 132 | 0.120 | |
| | 159 | 23 | 136 | 0.145 | 0.121 |
| 1, sphagnum moss | 94 | 19 | 75 | 0.202 | |
| | 85 | 45 | 40 | 0.529 | |
| | 96 | 33 | 63 | 0.344 | |
| | 71 | 42 | 29 | 0.591 | 0.417 |
| 2, sphagnum moss | 234 | 33 | 201 | 0.141 | |
| | 234 | 36 | 198 | 0.154 | |
| | 221 | 1 | 190 | 0.140 | |
| | 225 | 36 | 189 | 0.160 | 0.595 |
| 3, sphagnum moss | 289 | 34 | 261 | 0.117 | |
| | 279 | 35 | 248 | 0.125 | |
| | 281 | 37 | 249 | 0.132 | |
| | 291 | 36 | 262 | 0.124 | 0.125 |
| 4, sphagnum moss | 117 | 116 | 1 | 0.991 | |
| | 128 | 1287 | 0 | 1.000 | |
| | 137 | 137 | 0 | 1.000 | |
| | 133 | 132 | 1 | 0.992 | 0.996 |
| 5, sphagnum moss | 166 | 162 | 4 | 0.976 | |
| | 213 | 210 | 3 | 0.986 | |
| | 211 | 208 | 3 | 0.986 | |
| | 188 | 186 | 2 | 0.989 | 0.984 |
| 6, sphagnum moss | 76 | 73 | 3 | 0.961 | |
| | 70 | 68 | 2 | 0.971 | |
| | 95 | 92 | 3 | 0.968 | |
| | 78 | 77 | 1 | 0.987 | 0.972 |
| 7, maidenhair fern | 89 | 84 | 5 | 0.944 | |
| | 84 | 82 | 2 | 0.976 | |
| | 90 | 87 | 3 | 0.967 | |
| | 94 | 91 | 3 | 0.968 | 0.964 |
| 8, tree fern | 162 | 149 | 13 | 0.920 | |
| | 143 | 131 | 12 | 0.916 | |
| | 146 | 134 | 12 | 0.918 | |
| | 155 | 142 | 13 | 0.916 | 0.918 |
| 9, club moss | 111 | 57 | 54 | 0.514 | |
| | 111 | 60 | 51 | 0.541 | |
| | 115 | 61 | 54 | 0.530 | |
| | 109 | 59 | 50 | 0.541 | 0.532 |

Figure 7:
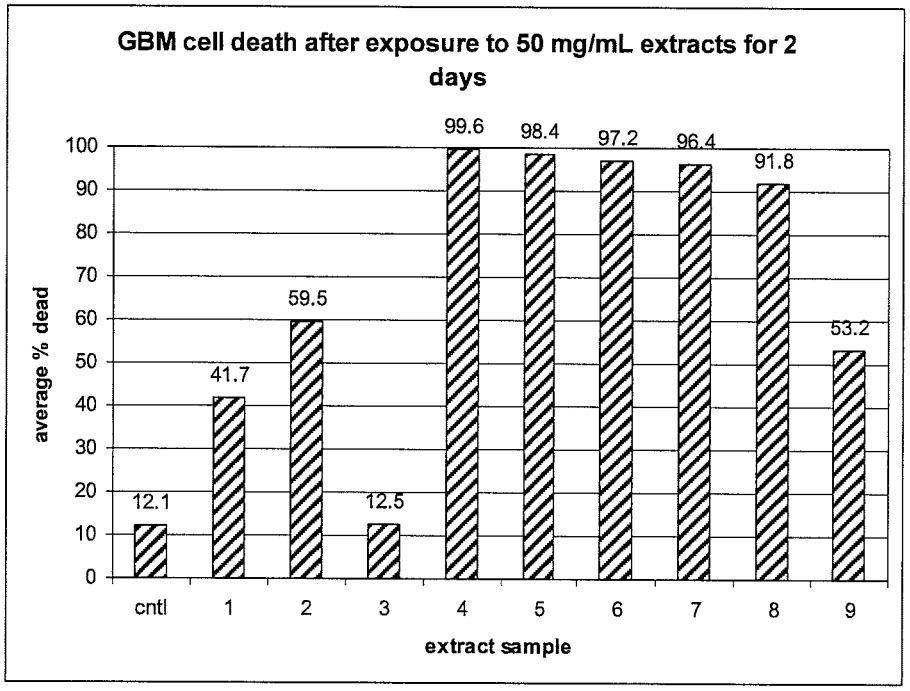
FIG. 7 is a graph of GBM cancer cell death after exposure to extract samples.

The results are graphically shown in FIG. 7.
Glioblastoma Multiforme Cell Recovery after Two Day Exposure to 50 mg/mL Extracts from Moss or Ferns Followed by Replating and 24 Hour Recovery.

The samples of Table I were replated and incubated for 24 hours. After the 24 hour incubation the samples were assayed. Results of the recovery assay are shown in the Table below.

TABLE 10

GBM cell 24 hour recovery after 2 day extract exposure

| extract sample | Total | Dead | Alive | % Dead | Ave. % Dead | % Alive | Ave. % Alive |
|---|---|---|---|---|---|---|---|
| control | 24 | 3 | 21 | 0.125 | | .875 | |
| | 20 | 2 | 18 | 0.100 | | .900 | |
| | 23 | 3 | 20 | 0.130 | | .870 | |
| | 26 | 4 | 21 | 0.154 | 0.127 | .808 | 0.863 |
| 1, *sphagnum* moss | 17 | 10 | 7 | 0.589 | | 0.412 | |
| | 18 | 12 | 6 | 0.667 | | 0.333 | |
| | 15 | 8 | 7 | 0.533 | | 0.467 | |
| | 18 | 10 | 8 | 0.566 | 0.586 | 0.445 | 0.414 |
| 2, *sphagnum* moss | 20 | 10 | 10 | 0.500 | | 0.500 | |
| | 19 | 7 | 12 | 0.368 | | 0.632 | |
| | 23 | 9 | 14 | 0.391 | | 0.609 | |
| | 17 | 6 | 11 | 0.353 | 0.403 | 0.647 | 0.597 |
| 3, *sphagnum* moss | 28 | 10 | 18 | 0.357 | | 0.643 | |
| | 30 | 15 | 15 | 0.500 | | 0.500 | |
| | 37 | 11 | 26 | 0.297 | | 0.703 | |
| | 29 | 9 | 20 | 0.310 | 0.366 | 0.689 | 0.634 |
| 4, *sphagnum* moss | 57 | 57 | 0 | 1.000 | | 0.000 | |
| | 64 | 63 | 1 | 0.984 | | 0.016 | |
| | 59 | 59 | 0 | 1.000 | | 0.000 | |
| | 65 | 65 | 0 | 1.000 | 0.996 | 0.000 | 0.004 |
| 5, *sphagnum* moss | 75 | 75 | 0 | 1.000 | | 0.000 | |
| | 78 | 78 | 0 | 1.000 | | 0.000 | |
| | 67 | 67 | 0 | 1.000 | | 0.000 | |
| | 70 | 69 | 1 | 0.986 | 0.996 | 0.014 | 0.004 |
| 6, *sphagnum* moss | 29 | 24 | 5 | 0.828 | | 0.172 | |
| | 29 | 25 | 4 | 0.862 | | 0.138 | |
| | 29 | 26 | 3 | 0.897 | | 0.103 | |
| | 30 | 25 | 5 | 0.833 | 0.855 | 0.167 | 0.145 |
| 7, maidenhair fern | 34 | 30 | 4 | 0.882 | | 0.118 | |
| | 34 | 31 | 3 | 0.912 | | 0.088 | |
| | 37 | 33 | 4 | 0.892 | | 0.108 | |
| | 39 | 35 | 4 | 0.897 | 0.896 | 0.103 | 0.104 |
| 8, tree fern | 35 | 33 | 2 | 0.943 | | 0.057 | |
| | 41 | 37 | 4 | 0.902 | | 0.098 | |
| | 46 | 41 | 5 | 0.891 | | 0.109 | |
| | 42 | 38 | 4 | 0.905 | 0.910 | 0.095 | 0.090 |
| 9, club moss | 23 | 11 | 12 | 0.478 | | 0.522 | |
| | 22 | 7 | 15 | 0.318 | | 0.682 | |
| | 22 | 8 | 14 | 0.364 | | 0.636 | |
| | 22 | 7 | 16 | 0.318 | 0.369 | 0.727 | 0.642 |

Figure 8:
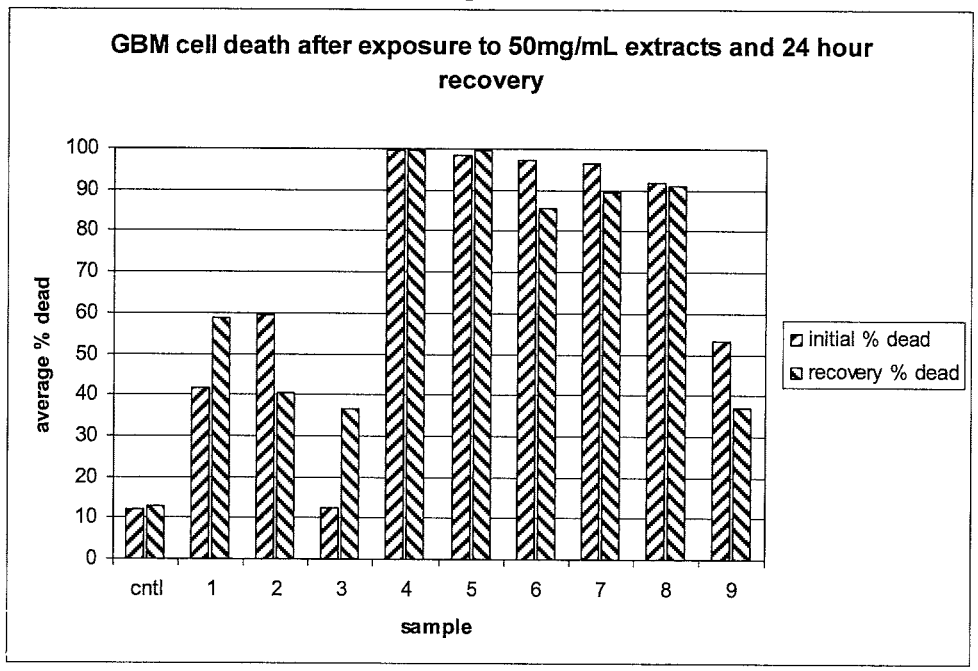
FIG. 8 is a graph of GBM cancer cell death after exposure to extract samples.

The results are graphically shown in FIG. 8.
Glioblastoma Multiforme (Monolayer Culture) Cell Death after 20 Hour Exposure to 50 mg/mL Extracts from Moss, Fern and Lichen.

TABLE 11

GBM cell death, 20 hour exposure, 50 mg/mL extract samples

| extract sample | Total | Dead | Alive | % Dead | Ave. % Dead |
|---|---|---|---|---|---|
| control | 29 | 4 | 24 | 0.138 | |
| | 25 | 3 | 22 | 0.120 | |
| | 28 | 4 | 24 | 0.143 | |
| | 23 | 2 | 21 | 0.087 | 0.158 |
| 10, club moss | 16 | 7 | 9 | 0.438 | |
| | 22 | 8 | 14 | 0.364 | |
| | 23 | 7 | 16 | 0.304 | |
| | 31 | 9 | 22 | 0.290 | 0.349 |
| 11, club moss | 24 | 10 | 14 | 0.417 | |
| | 35 | 17 | 18 | 0.486 | |

TABLE 11-continued

GBM cell death, 20 hour exposure, 50 mg/mL extract samples

| extract sample | Total | Dead | Alive | % Dead | Ave. % Dead |
|---|---|---|---|---|---|
|  | 14 | 5 | 9 | 0.357 |  |
|  | 19 | 6 | 13 | 0.316 | 0.394 |
| 12, club moss | 15 | 7 | 8 | 0.467 |  |
|  | 17 | 11 | 6 | 0.647 |  |
|  | 14 | 9 | 5 | 0.643 |  |
|  | 24 | 14 | 10 | 0.583 | 0.585 |
| 13, Christmas fern | 13 | 10 | 3 | 0.769 |  |
|  | 9 | 9 | 9 | 1.000 |  |
|  | 14 | 11 | 3 | 0.786 |  |
|  | 11 | 10 | 1 | 0.909 | 0.866 |
| 14, lichen | 18 | 7 | 11 | 0.389 |  |
|  | 19 | 5 | 14 | 0.263 |  |
|  | 13 | 4 | 9 | 0.308 |  |
|  | 37 | 11 | 16 | 0.297 | 0.314 |

Figure 9:
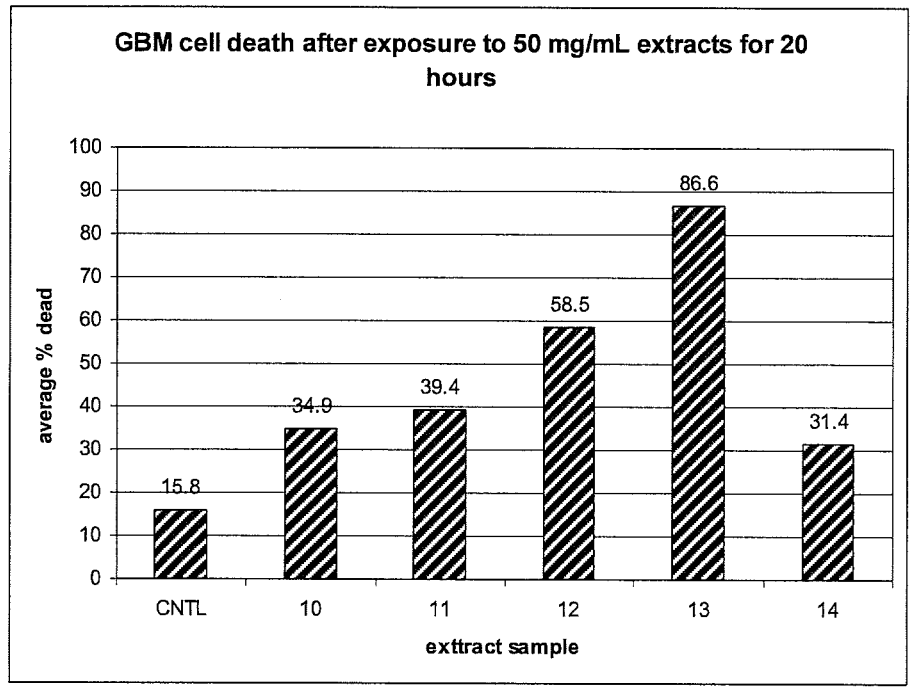
FIG. 9 is a graph of GBM cancer cell death after exposure to extract samples.

The results are graphically shown in FIG. 9.

Chemoprevention of Glioblastoma Multiforme Cells after 20 Hour Exposure to 50 mg/mL Extract Samples from Moss, Fern and Lichen.

Glioblastoma multiforme cells and an extract sample (50 mg/mL) were added at the same time to a dish coated with a laminin support. After twenty hours the dishes were checked for cell death. The data is summarized in the Table below.

TABLE 12 chemoprevention of GBM tumor formation and cell death after 20 hour exposure to 50 mg/mL extracts

| extract sample | Total | Dead | Alive | % Dead | Ave. % Dead |
|---|---|---|---|---|---|
| control | 49 | 10 | 39 | 0.204 |  |
|  | 51 | 12 | 39 | 0.235 |  |
|  | 52 | 11 | 41 | 0.211 |  |
|  | 50 | 10 | 40 | 0.200 | 0.213 |
| 10, club moss | 77 | 20 | 57 | 0.260 |  |
|  | 57 | 17 | 37 | 0.298 |  |
|  | 55 | 16 | 39 | 0.291 |  |
|  | 70 | 18 | 52 | 0.257 | 0.276 |
| 11, club moss | 56 | 19 | 37 | 0.339 |  |
|  | 41 | 12 | 29 | 0.293 |  |
|  | 49 | 18 | 31 | 0.367 |  |
|  | 40 | 14 | 26 | 0.350 | 0.337 |
| 12, club moss | 64 | 45 | 19 | 0.703 |  |
|  | 64 | 43 | 21 | 0.672 |  |
|  | 46 | 39 | 7 | 0.848 |  |
|  | 31 | 29 | 2 | 0.936 | 0.790 |
| 13, Christmas fern | 74 | 47 | 27 | 0.635 |  |
|  | 36 | 24 | 12 | 0.667 |  |
|  | 83 | 40 | 43 | 0.482 |  |
|  | 60 | 34 | 26 | 0.567 | 0.588 |
| 14, lichen | 87 | 50 | 37 | 0.575 |  |
|  | 67 | 25 | 42 | 0.373 |  |
|  | 67 | 21 | 46 | 0.313 |  |
|  | 69 | 23 | 46 | 0.333 | 0.399 |
| 4, sphagnum moss | 40 | 10 | 30 | 0.250 |  |
|  | 33 | 8 | 25 | 0.242 |  |
|  | 34 | 10 | 24 | 0.294 |  |
|  | 27 | 7 | 20 | 0.259 | 0.261 |
| 5, sphagnum moss | 85 | 78 | 7 | 0.918 |  |
|  | 84 | 80 | 4 | 0.952 |  |
|  | 81 | 76 | 5 | 0.938 |  |
|  | 82 | 76 | 6 | 0.927 | 0.934 |
| 6, sphagnum moss | 87 | 84 | 3 | 0.966 |  |
|  | 91 | 86 | 5 | 0.945 |  |
|  | 85 | 82 | 3 | 0.965 |  |
|  | 81 | 77 | 4 | 0.951 | 0.956 |

Figure 10:
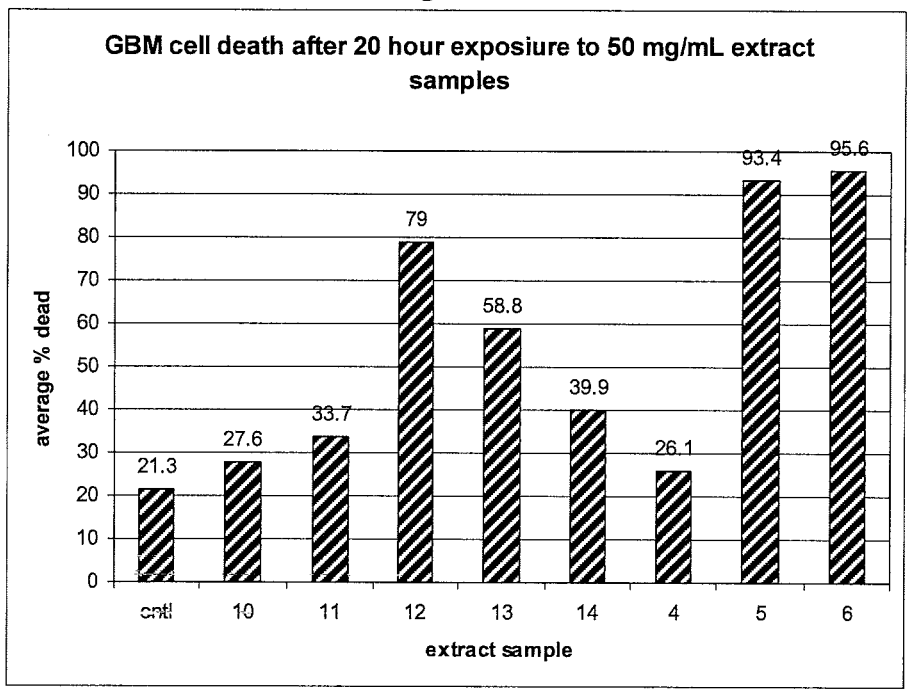
FIG. 10 is a graph of GBM cancer cell death after exposure to extract samples.

The results are graphically shown in FIG. 10. FIG. 10 illustrates that extracts prepared from numerous species of mosses and ferns block solid tumor formation of the brain cancer glioblastoma multiforme on laminin extracellular matrix and induce cell death. Most potent effects were observed for extracts 5, 6 and 12.

Effect of Extract Samples on Glioblastoma Multiforme Three Dimensional Multicellular Tumor Spheroid (MTS) Cultures.

Figure 11:
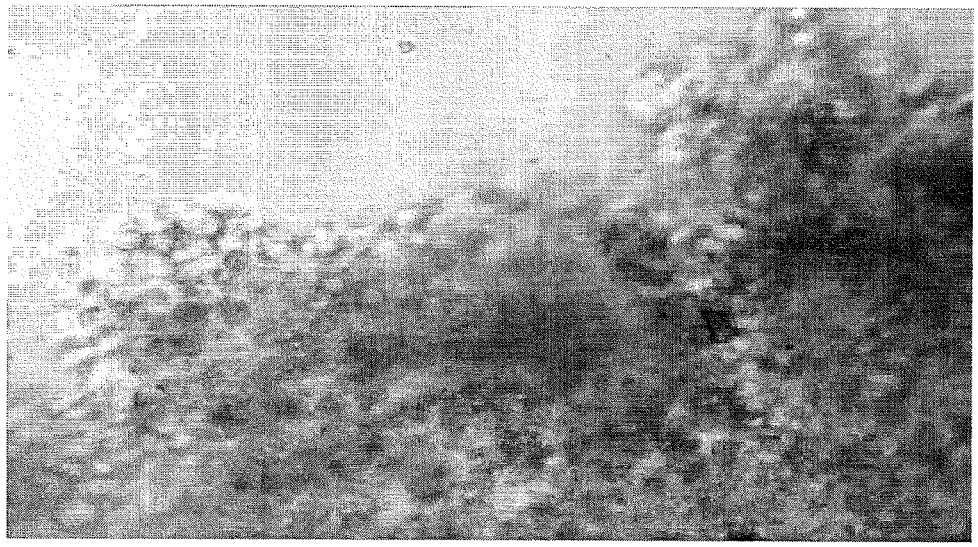
FIG. 11 is a microphotograph of GBM cancer cells formed into multi-cellular tumor spheroids (MTS).

Glioblastoma multiforme (DRTG-GBM) cells were cultured for several days on 1% agarose matrix. The 1% agarose matrix prevents cell-to-substrate attachment and facilitates formation of the glioblastoma multiforme cells into three dimensional multicellular tumor spheroids (MTS). These multi-cellular tumor spheroid aggregates measure from 1-3 mm in diameter and share many similarities with in vivo solid tumors, are comparable to the formation of in vivo micrometastatic lesions and provide results that are believed to be representative of what can be expected during treatment of in vivo solid tumors. The cells were not treated with extract sample. FIG. 11 shows the glioblastoma multiforme in vitro three dimensional multicellular tumor spheroids (MTS).

Figure 12:
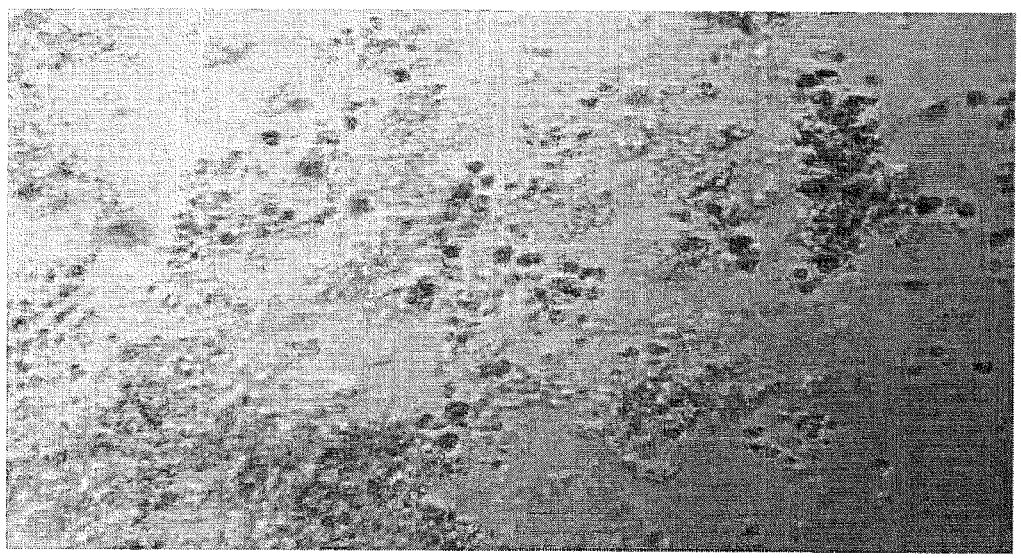
FIG. 12 is a microphotograph of GBM cancer cells formed into multi-cellular tumor spheroids (MTS) after treatment with an extract sample.

FIG. 12 shows glioblastoma multiforme (DRTG-GBM) cells cultured on 1% agarose matrix as in FIG. 11. The cells were treated with extract sample 3 (50 mg/mL). No in vitro three dimensional multicellular tumor spheroids formed after treatment with the extract sample.

Effect of Extract Samples on Glioblastoma Multiforme Monolayer Cultures.

Figure 13:
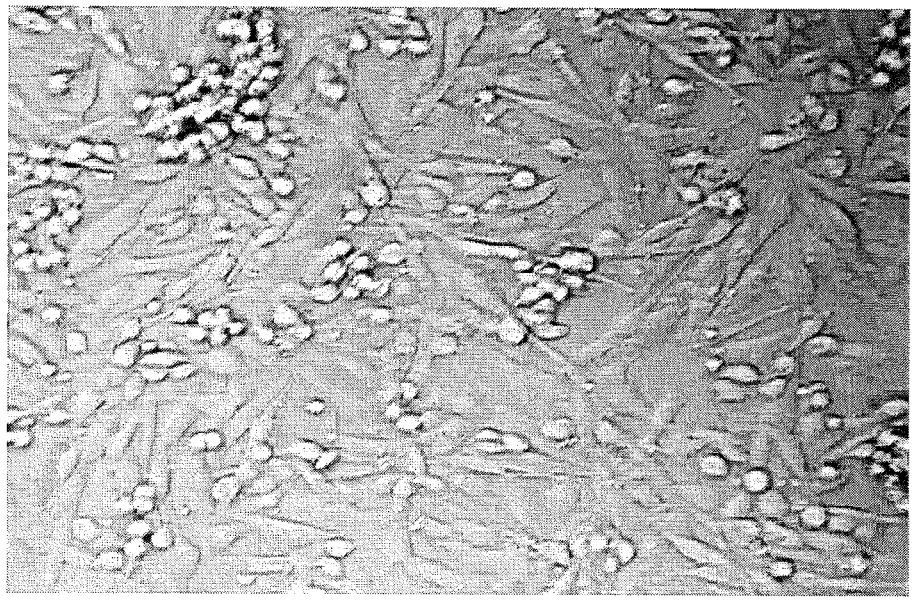
FIG. 13 is a microphotograph of GBM cancer cells cultured on a laminin matrix.

FIG. 13 shows glioblastoma multiforme (DRTG-GBM) cells cultured for 24 hours on a laminin extracellular matrix. The cells were not treated with extract sample. The cells form a confluent monolayer attached to the laminin matrix.

Figure 14:
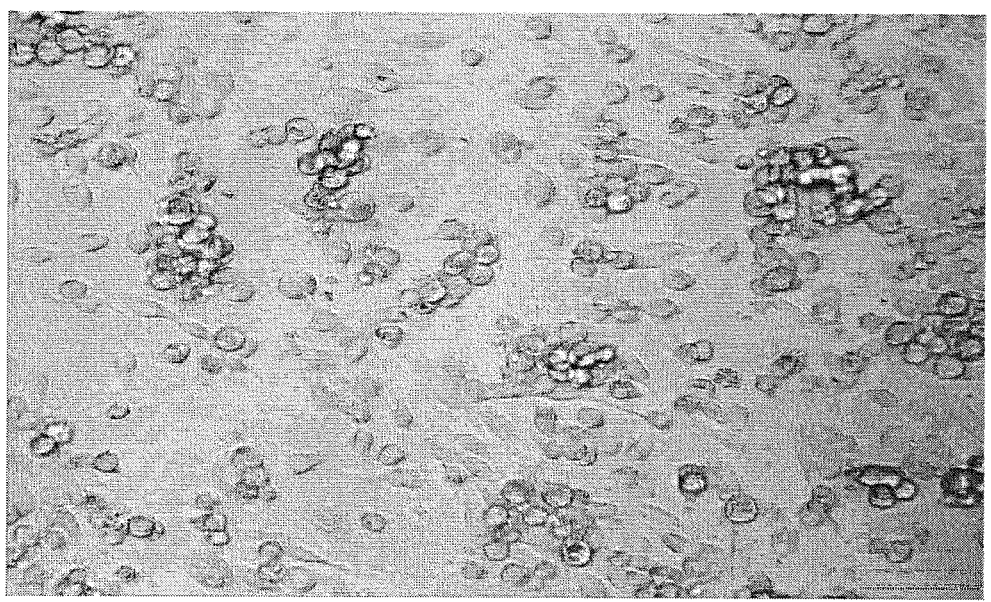
FIG. 14 is a microphotograph of GBM cancer cells cultured on a laminin matrix after treatment with an extract sample.

FIG. 14 shows glioblastoma multiforme (DRTG-GBM) cells cultured on a laminin extracellular matrix as in FIG. 13. The cells were treated with extract sample 11 (50 mg/mL). The cells are rounded up, see arrow, and are not attached to the laminin matrix.

Figure 15:
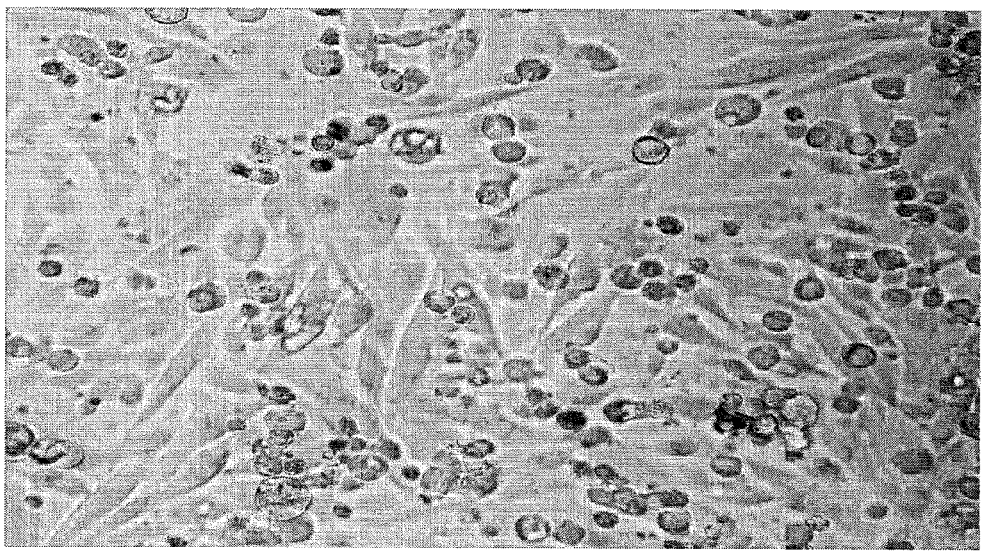
FIG. 15 is a microphotograph of GBM cancer cells cultured as monolayers.

FIG. 15 shows a glioblastoma multiforme (DRTG-GBM) cells cultured as monolayers. The cells were not treated with extract sample.

Figure 16:
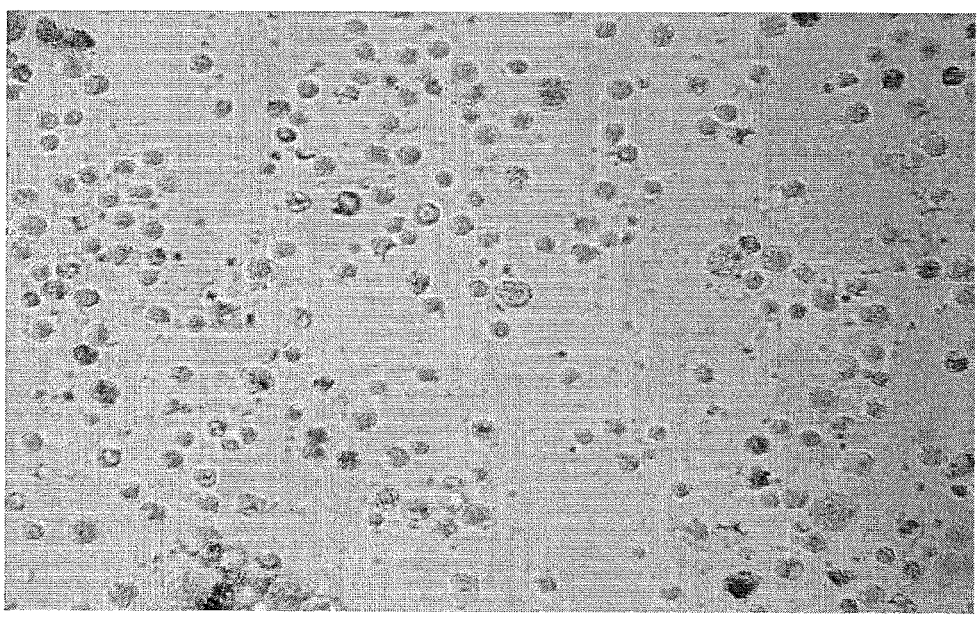
FIG. 16 is a microphotograph of GBM cancer cells cultured as monolayers after treatment with an extract sample.

FIG. 16 shows glioblastoma multiforme (DRTG-GBM) cells cultured as in FIG. 15. The cells were treated with an extract sample. The cells are rounded up and detached from the substrate.

Primary (SW620) and Metastatic (SW480) Colon Cancer Cell Death after 3 Day Exposure to 25 mg/mL Extract Samples from Moss, Fern and Lichen.

An extract sample (25 mg/mL) was added to dishes containing primary (SW620) and metastatic (SW480) colon cancer cells. After three days the dishes were checked for cell death. The data is summarized in the Table below.

TABLE 13

| extract sample | primary colon cancer % dead cells | metastatic colon cancer % dead cells |
|---|---|---|
| no agent (control) | 17 | 7 |
| 10, club moss | 49 | 100 |
| 11, club moss | 38 | 63 |
| 12, club moss | 85 | 100 |
| 13, fern | 32 | 41 |
| 14, lichen | 76 | 100 |

Figure 17:
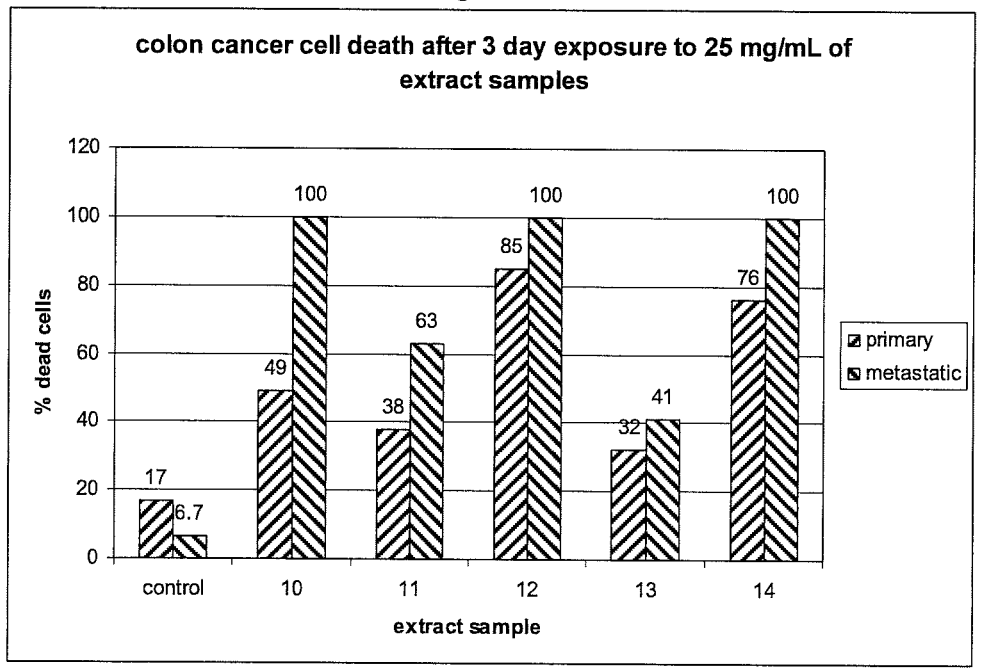
FIG. 17 is a graph of colon cancer cell death after exposure to extract samples.

The results are graphically shown in FIG. 17. The results illustrate extract samples 10, 12 and 14 have a higher anti-tumor activity against primary SW620 and metastatic SW480 colon cancer while extract samples 11 and 13 produce a lower, but significant, anti-tumor activity. The results also illustrate that the extracts are differentially more active against metastatic SW480 colon cancer then to primary SW620 colon cancer.

Primary (SW620) and Metastatic (SW480) Colon Cancer Cell Death after 24 Hour Exposure to 50 mg/mL Extract Samples from Moss, Fern and Lichen.

An extract sample (50 mg/mL) was added to dishes containing primary (SW620) and metastatic (SW480) colon cancer cells. After 24 hours the dishes were checked for cell death. The data is summarized in the Table below.

TABLE 14

| extract sample | primary colon cancer % dead cells | metastatic colon cancer % dead cells |
|---|---|---|
| no agent (control) | 22 | 6 |
| 10, club moss | 38 | 36 |
| 11, club moss | 100 | 36 |
| 12, club moss | 100 | 100 |
| 13, fern | 36 | 17 |
| 14, lichen | 34 | 29 |

Figure 18:
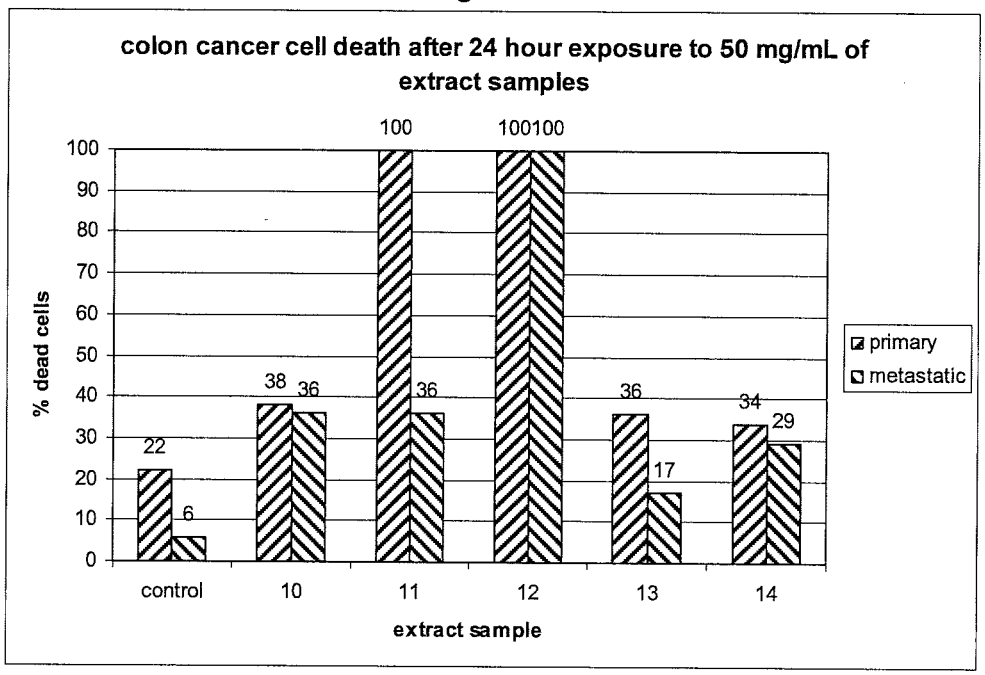
FIG. 18 is a graph of colon cancer cell death after exposure to extract samples.

The results are graphically shown in FIG. 18. The results illustrate extract samples 11 and 12 have a higher anti-tumor activity against primary SW620 and metastatic SW480 colon cancer while extract samples 10, 13 and 14 produce a lower, but significant, anti-tumor activity.

Primary Colon Cancer Cell Death after 24 Hour Exposure to 50 mg/mL Extract Samples from Moss and Lichen.

An extract sample (50 mg/mL) was added to dishes containing primary colon cancer cells. After 24 hours the dishes were checked for cell death. The data is summarized in the Table below.

TABLE 15 primary colon cancer cell death, 24 hour exposure

| extract sample | Total | Dead | Alive | % Dead | Ave. % Dead |
|---|---|---|---|---|---|
| 6, sphagnum moss | 76 | 76 | 0 | 1.000 | |
| | 81 | 81 | 0 | 1.000 | |
| | 73 | 73 | 0 | 1.000 | |
| | 79 | 79 | 0 | 1.000 | 1.000 |
| 10, club moss | 124 | 33 | 97 | 0.266 | |
| | 128 | 16 | 112 | 0.125 | |
| | 102 | 26 | 76 | 0.255 | |
| | 123 | 23 | 100 | 0.187 | 0.208 |
| 11, club moss | 120 | 39 | 81 | 0.325 | |
| | 117 | 41 | 76 | 0.350 | |
| | 121 | 44 | 77 | 0.364 | |
| | 121 | 39 | 82 | 0.322 | 0.340 |
| 12, club moss | 86 | 86 | 0 | 1.000 | |
| | 91 | 91 | 0 | 1.000 | |
| | 97 | 97 | 0 | 1.000 | |
| | 73 | 73 | 0 | 1.000 | 1.000 |
| 14, lichen | 142 | 79 | 63 | 0.556 | |
| | 141 | 81 | 60 | 0.574 | |
| | 115 | 71 | 44 | 0.617 | |
| | 103 | 72 | 31 | 0.699 | 0.612 |

Figure 19:
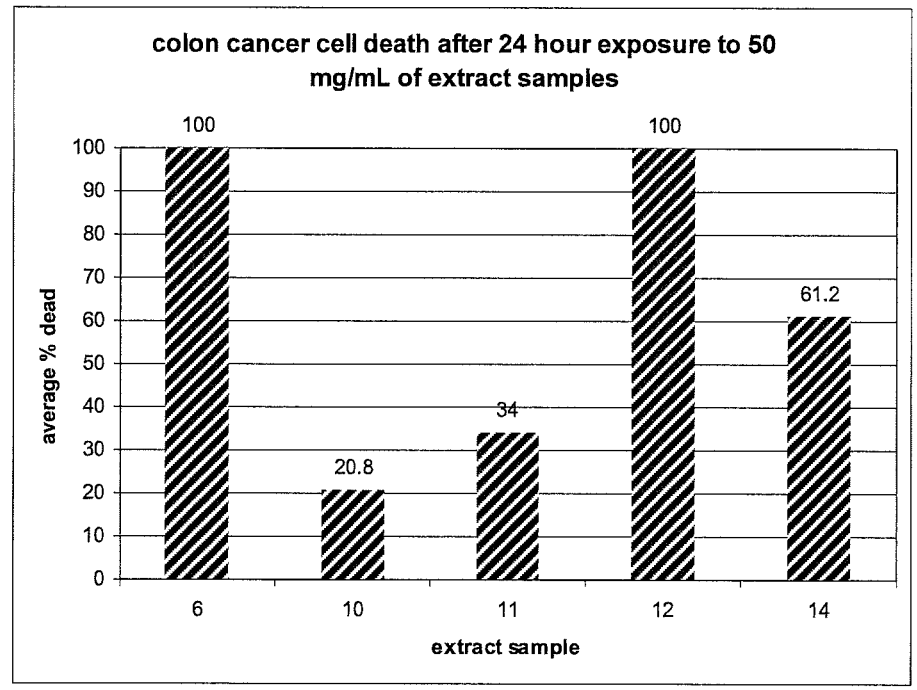
FIG. 19 is a graph of colon cancer cell death after exposure to extract samples.

The results are graphically shown in FIG. 19.

Metastatic Colon Cancer Cell Death (Adeno Lines) after 24 Hour Exposure to 50 mg/mL Extract Samples from Moss and Lichen.

An extract sample (50 mg/mL) was added to dishes containing metastatic colon cancer cells. After 24 hours the dishes were checked for cell death. The data is summarized in the Table below.

TABLE 16 metastatic colon cancer (Adeno line) cell death, 24 hour exposure

| extract sample | Total | Dead | Alive | % Dead | Ave. % Dead |
|---|---|---|---|---|---|
| 6, sphagnum moss | 45 | 40 | 5 | 0.889 | |
| | 41 | 37 | 4 | 0.902 | |
| | 41 | 38 | 3 | 0.927 | |
| | 46 | 41 | 5 | 0.891 | 0.902 |
| 10, club moss | 38 | 36 | 2 | 0.947 | |
| | 39 | 39 | 0 | 1.000 | |
| | 42 | 41 | 1 | 0.976 | |
| | 39 | 39 | 0 | 1.000 | 0.981 |
| 11, club moss | 44 | 30 | 14 | 0.682 | |
| | 21 | 14 | 7 | 0.667 | |
| | 34 | 24 | 10 | 0.706 | |
| | 28 | 22 | 6 | 0.786 | 0.710 |
| 12, club moss | 33 | 30 | 3 | 0.909 | |
| | 25 | 24 | 2 | 0.960 | |
| | 34 | 29 | 5 | 0.853 | |
| | 33 | 30 | 3 | 0.909 | 0.908 |
| 14, lichen | 37 | 35 | 2 | 0.946 | |
| | 38 | 36 | 2 | 0.947 | |
| | 42 | 39 | 3 | 0.929 | |
| | 34 | 34 | 0 | 1.000 | 0.955 |

Figure 20:
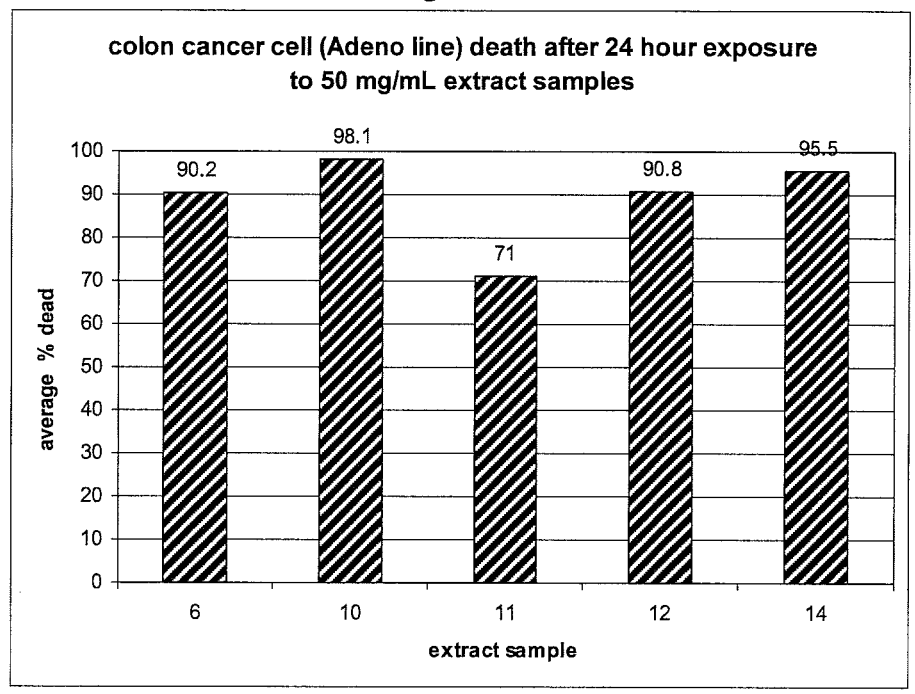
FIG. 20 is a graph of colon cancer cell death after exposure to extract samples.

The results are graphically shown in FIG. 20.

Effect of Extract Samples on Colon Cancer.

Figure 21:
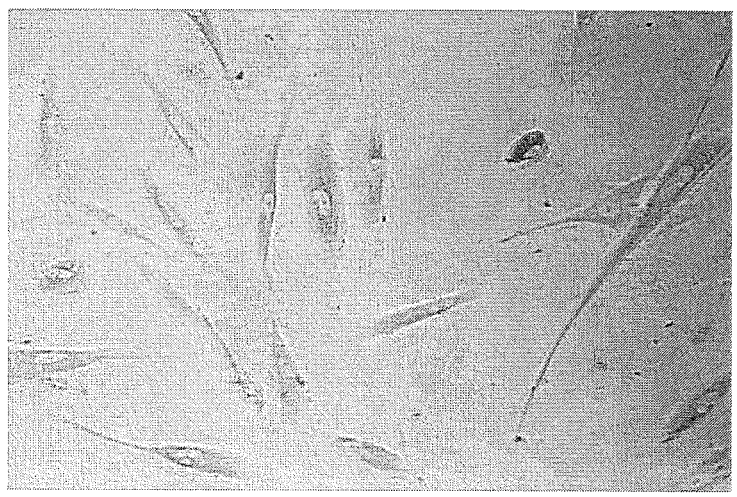
FIG. 21 is a microphotograph of non-cancerous colon cells after treatment with an extract sample.

FIG. 21 shows normal (non-cancerous) colon cells treated with an extract sample. The cells appear slightly stressed by treatment with the extract sample, although the cells remain attached to the substrate and viable in culture.

Figure 22:
FIG. 22 is a series of microphotographs illustrating the differential effect of an extract sample on colon cell lines correlated with degree of malignant transformation.
Figure 22:
Figure 22:
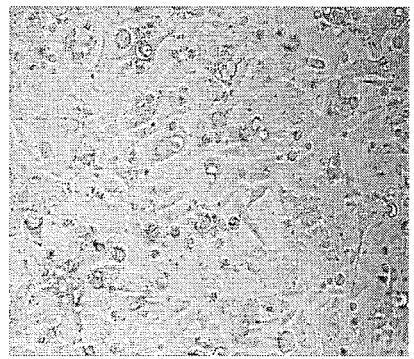
Figure 22:
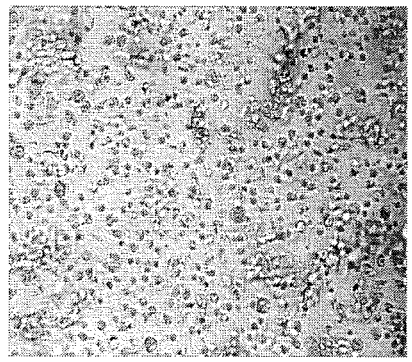
Figure 22:
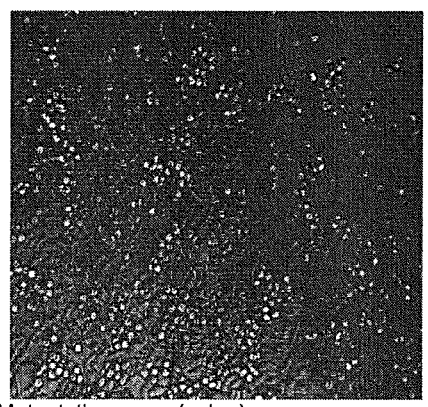
Figure 22:
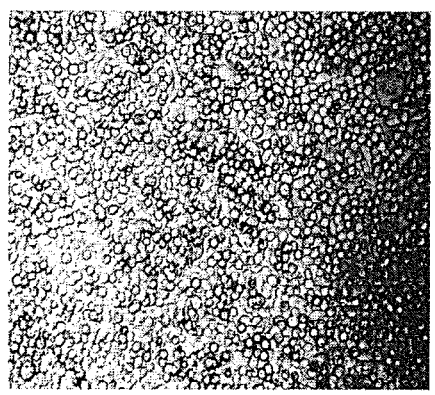

FIG. 22 illustrates the differential effects of extract sample 10 (club moss) on colon cell lines correlated with the degree of malignant transformation. There is a low level of effect on normal colon cells. The primary colon cancer cells exhibit more effect due to extract sample treatment and the metastatic colon cancer cells exhibit a higher level of effect due to extract sample treatment.

Figure 23:
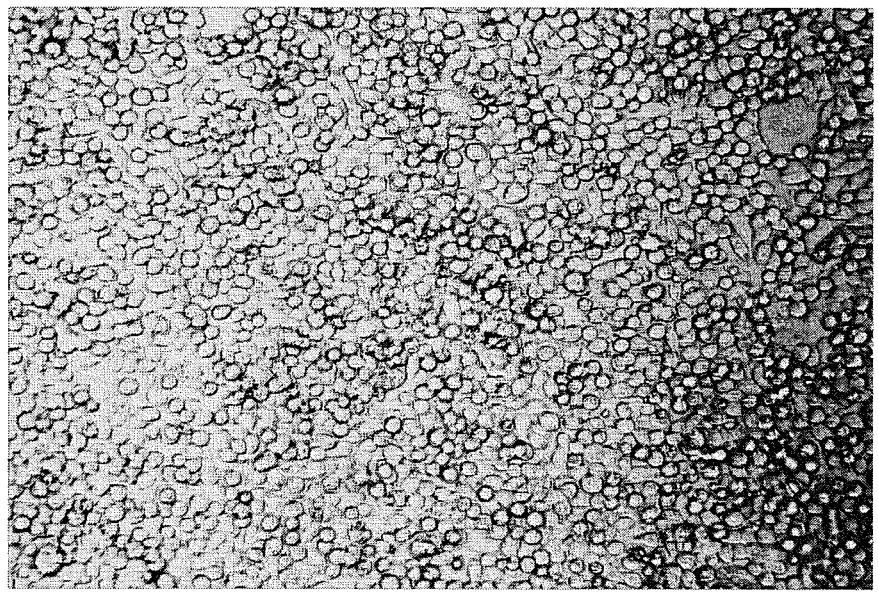
FIG. 23 is a microphotograph of metastatic colon cancer cells after treatment with an extract sample.

FIG. 23 illustrates a metastatic colon cancer cell line (SW620) after treatment with extract sample 10 (25 mg/mL). The colon cancer cells are rounded up and detached from the substrate. This figure indicates that this cell line after treatment has lost culture viability.

The results indicate that the extract samples have a differential effect on colon cells. Normal colon cells exhibit only a low level effect after treatment with extract samples while malignant colon tumor cells are differentially sensitive to treatment with extract samples. The extract samples are prepared from materials that are non-toxic. It is believed that the extract samples will have a low level of toxicity to normal cells in general.

Effect of Extract Samples on Cancer Cell Cytoskeleton.

Figure 24:
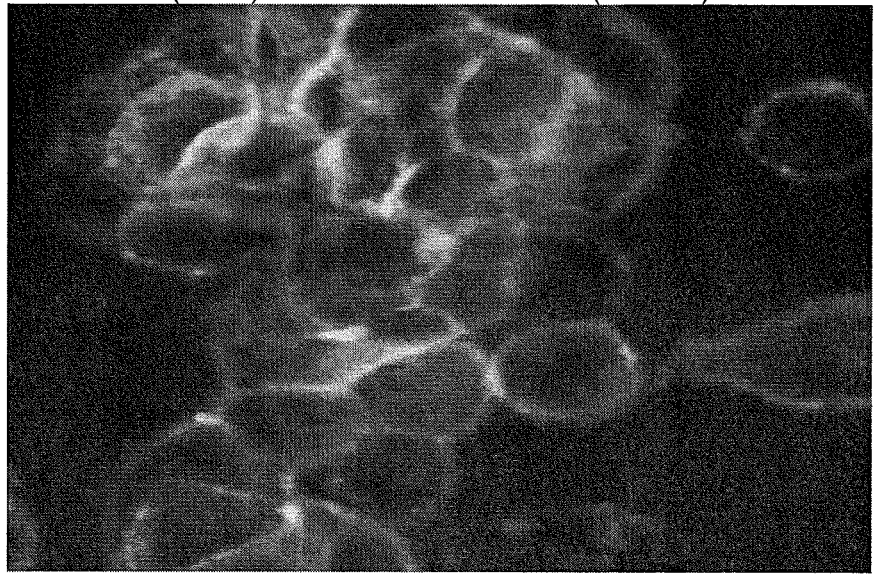
FIG. 24 is a confocal laser microphotograph of untreated metastatic colon cancer cells.
Figure 25:
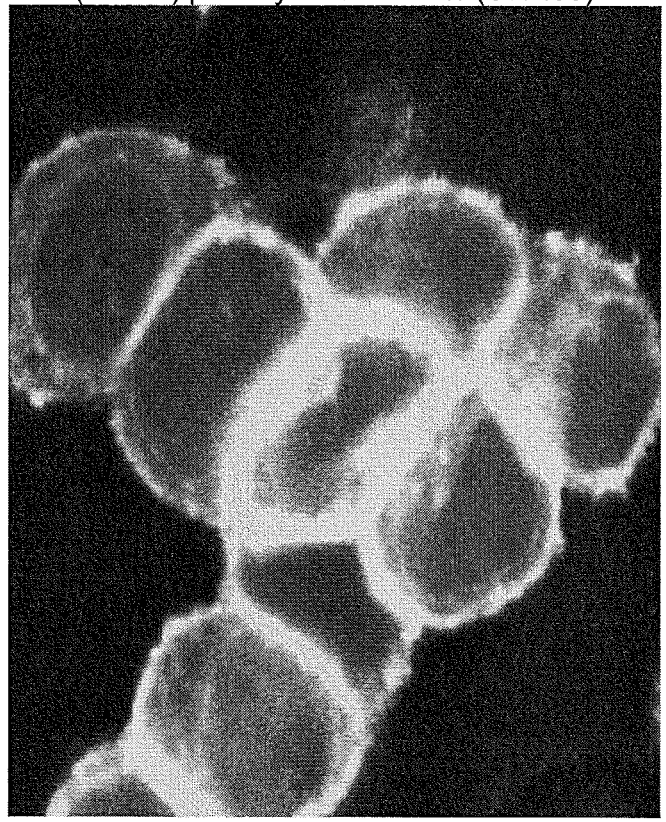
FIG. 25 is a confocal laser microphotograph of untreated primary colon cancer cells.

FIGS. 24 and 25 show confocal laser microscopy images of human metastatic (SW260) (400×) and primary (SW480) (1000×) colon cancer cell lines (untreated) after staining with phalloidin stain. This stains actin filaments in the cells. The stained actin filaments, sample shown by arrow, are localized at the cell periphery to form a cell cytoskeleton.

Figure 26:
FIG. 26 is a confocal laser microphotograph of primary colon cancer cells after treatment with an extract sample.

FIG. 26 shows confocal laser microscopy images of human primary (SW480) (1000×) colon cancer cell lines after treatment with extract sample 10 (50 mg/mL) for 24 hours at 37° C., removal of media and extract, rinsing and staining with phalloidin stain.

Figure 27:
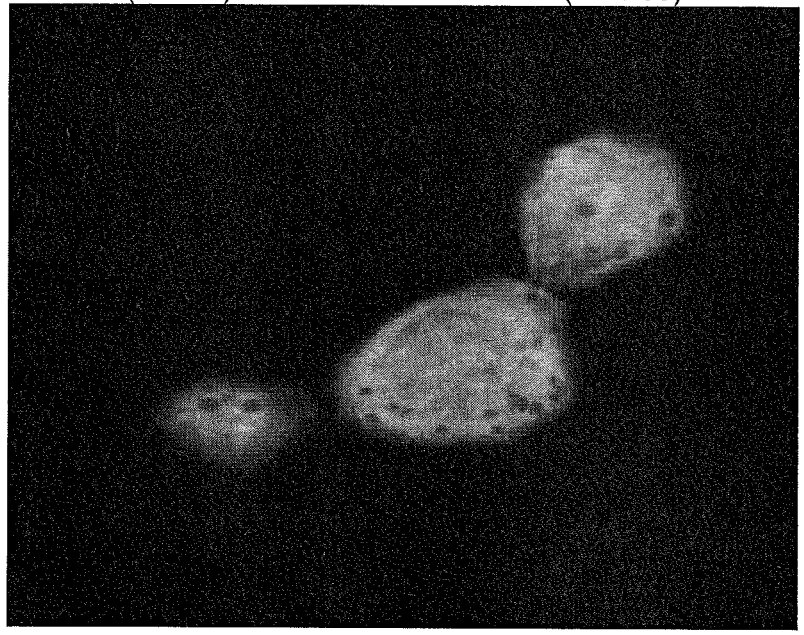
FIG. 27 is a confocal laser microphotograph of metastatic colon cancer cells after treatment with an extract sample.

FIG. 27 shows confocal laser microscopy images of human metastatic (SW260) (1000×) colon cancer cell lines after treatment with extract sample 11 (50 mg/mL) for 24 hours at 37° C., removal of media and extract, rinsing and staining with phalloidin stain.

Additional testing was done using extract samples 6, 10, 11 and 12 on both primary and metastatic colon cancer cells. In all testing the micrographs show that the extract sample has disordered the actin filaments, see arrows, away from the cell periphery, thereby destroying the cell cytoskeleton.

Figure 28:
FIG. 28 is a confocal laser microphotograph of untreated GBM cancer cells.

FIG. 28 show confocal laser microscopy images of a human glioblastoma multiforme brain tumor cell line (40×) after staining with phalloidin stain. This stains actin filaments in the cells. The fluorescently stained actin filaments, sample shown by arrow, are localized at the cell periphery to form a cell cytoskeleton.

Figure 29:
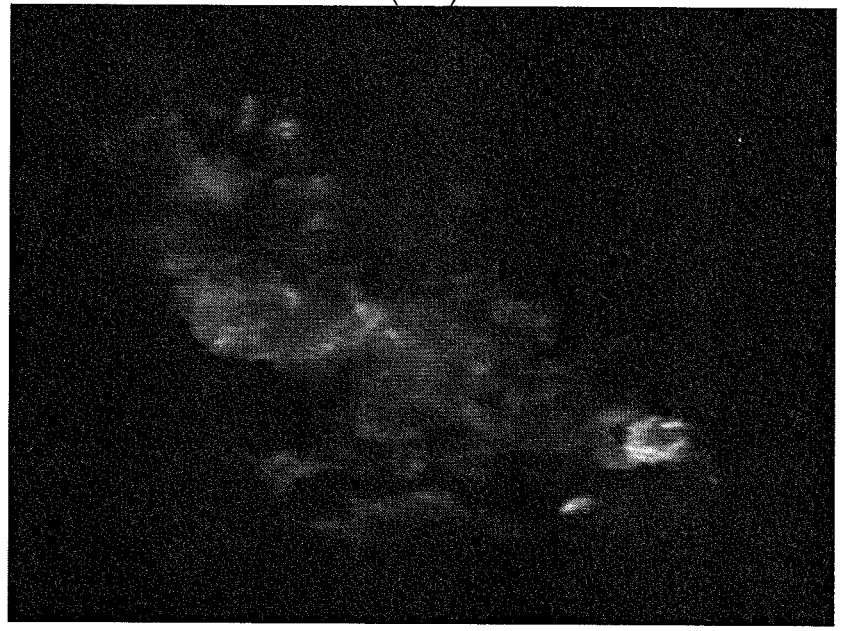
FIG. 29 is a confocal laser microphotograph of GBM cancer cells after treatment with an extract sample.

FIG. 29 show confocal laser microscopy images of a human glioblastoma multiforme brain tumor cell line (40×) after treatment with an extract sample and staining with phalloidin stain reagent. The micrographs show that the extract sample has disordered the actin filaments, see arrows, away from the cell periphery, thereby destroying the cell cytoskeleton.

FIGS. 24 to 29 suggest that the cancer cell cytoskeleton/FAK complex plays a role in mediating the cell-to-cell contacts critical to solid tumor formation, a process directly linked to tumor cell viability and tumor cell survival. The disclosed extract samples appear to target actin filaments and the cancer cell cytoskeleton to provide a useful therapeutic effect across a broad range of different cancer lines.

Based on studies with normal colon and lung tissue it appears that extracts are less toxic to normal cells than cancer cells based on a visual qualitative assessment of cell viability and attachment.

Assay for Thermal Degradation of Extract Samples.

In order to determine whether or not proteins or other thermally sensitive components were involved in the effectiveness of the extracts on human malignancies, the following technique was utilized to break down the proteins prior to testing for effectiveness.

After the extract samples were spun down in the 50 mL centrifuge tubes, they were placed into 1.5 mL tubes, and spun down in the micro centrifuge. The extract samples were placed in a floating tube rack in a 70° C. water bath for 20 minutes. After 20 minutes in the water bath the samples were transferred to an ice bath for 5 minutes before use or further storage at 4° C.

Exposure to 70° C. did not significantly affect the anti-cancer properties of the extract samples.

Preparation of Plant Extracts Using Different Solvents.

A plant extract homogenate from a single fern species (extract sample 13) further extracted with a range of solvents having differing polarities, including ethanol; methanol; isopropanol; dimethylsulfoxide (DMSO); and phosphate buffered saline (PBS). The anti-cancer activity of each solvent preparation was then tested against a human glioblastoma tumor cell line. A photograph was taken after exposure of the GBM cells to each extract and to the solvent alone. The photographs were compared and ranked based on visual interpretation of the number of dead GBM cells in each test.

The results indicate that plant extracts display greater anti-cancer activity than the solvents alone. The results indicate that plant extracts display greater activity when made using less polar solvents, including dimethylsulfoxide (DMSO) and methanol and a lower activity when made using more polar solvents such as water or phosphate buffered saline (PBS).

Combinations of Plant Extracts with Additional Therapeutic Agents as a Therapeutic Treatment of Glioblastoma Multiform.

As used herein a therapeutic agent is an agent exhibiting cytotoxic activity to cancer cells and does not include non-cytotxically active materials, for example, an excipient, vehicle, adjuvant, flavoring, colorant or preservative. A therapeutic agent would include a material or materials known or believed to have cytotoxic properties with respect to cancer cells, for example, carmustine, berberine, curcumin, caffeic acid phenyl ester (CAPE), abscisic acid, 5-fluorouracil or gemcitabine.

The standard chemotherapeutic drug recommended to treat Glioblastoma Multiforme (GBM) is 1,3-bis(2-chloroethyl)-1-nitrosourea, more commonly known as BCNU or carmustine. Carmustine is a nitrosourea and an alkylating agent capable of crossing the blood-brain barrier. Carmustine works by alkylating and cross linking DNA strands thereby inhibiting cell proliferation. Intravenous administration of carmustine has serious side effects, including a decrease of bone marrow blood cells, lung damage and death. Further, carmustine applied in time release fashion to the tumor site only increased the mean survival rate from 11.6 months to 13.9 months.

Carmustine, berberine, curcumin, caffeic acid phenyl ester (CAPE), abscisic acid and a extract sample 19 (fern) were used, singly and in various combinations, to assess their potential effectiveness in promoting in vitro cell death responses in a malignant GBM cell line (ATCC crl-2020). Two different culture models were used in these experiments. The majority of vertebrate cells cultured in vitro grow as monolayers on an artificial substrate, as is the case with GBM cells. Live cells attach to the bottom of a tissue culture plate where they proliferate until the surface is confluent with cells. While this standard model is useful for determining the effects of treatments on tumor cells, monolayers do not completely represent the characteristics of in vivo three dimensional solid tumors. The three dimensional structure of solid tumors makes such tumors more resistant to treatment than a GBM cell monolayer culture. To more closely approximate in vivo conditions a multi-cellular tumor spheroid (MTS) model was used. In this model GBM cells were cultured on a 1% agarose matrix in a 24 well tissue culture dish to form multi cellular aggregates. These multi-cellular tumor spheroid aggregates share many similarities with in vivo solid tumors and provide results that are believed to be representative of what can be expected during treatment of in vivo solid tumors. Trypan blue staining and microscopic observation was used to assess cell viability after treatment.

Single agent treatment of GBM three dimensional multi-cellular tumor spheroid (MTS) cell cultures.

A GBM monolayer culture plate was treated with moderately low concentrations of carmustine (50 μM dose); curcumin (20 μM dose); CAPE (20 μM dose); ABA (400 μM dose) and extract sample 19 (10 mg/mL dose). The treated cultures were incubated for 12 hours at 38° C. and assayed. The dosing conditions were sub-optimal dosing conditions designed to allow better assessment of the combined agent results. Viability for each treated culture was 100%.

A GBM multicellular tumor spheroid (MTS) culture plate was treated with moderately low concentrations of carmustine (50 μM dose); curcumin (20 μM dose); CAPE (20 μM dose); ABA (400 μM dose) and extract sample 19 (10 mg/mL dose). The treated cultures were incubated for 24 hours at 38° C. and assayed. The dosing conditions were designed to represent sub-optimal dosing conditions.

When used alone carmustine produced only low level cytotoxicity in GBM monolayer and MTS cell cultures, even at the highest doses tested. Short term and low dose treatment with curcumin; CAPE; ABA or extract sample 13 used alone failed to produce significant cytotoxic responses in either the GBM monolayer or MTS cell cultures.

Multiple agent treatment of GBM three dimensional multicellular tumor spheroid (MTS) cell cultures.

A GBM multicellular tumor spheroid (MTS) culture plate was treated with different two agent and three agent combinations including curcumin and extract sample 13; carmustine and extract sample 13; carmustine and curcumin; and carmustine and curcumin and extract sample 13. The agent concentrations were the same as in the single agent testing (carmustine (50 μM dose); curcumin (20 μM dose); CAPE (20 μM dose); ABA (400 μM dose) and extract sample 13 (10 mg/mL dose).

The treated cultures were incubated for 24 hours at 38° C. and assayed. The dosing conditions were designed to represent sub-optimal dosing conditions. The results are shown in the Table below.

TABLE 17

| agent combination | % dead cells |
| --- | --- |
| no agent (control) | 18 |
| curcumin and extract sample 13 | 11 |
| carmustine and extract sample 13 | 14 |
| carmustine and curcumin | 28 |
| carmustine and curcumin and extract sample 1. | 47 |

Figure 30:
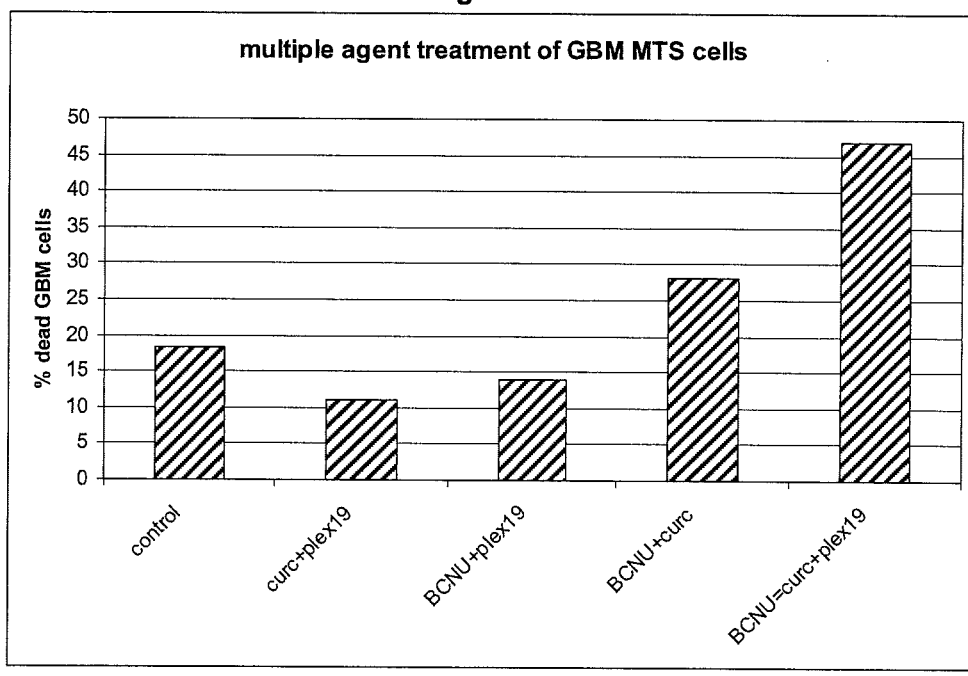
FIG. 30 is a graph of GBM cancer cell death after exposure to a formulation comprising a plurality of therapeutic agents.
Figure 31:
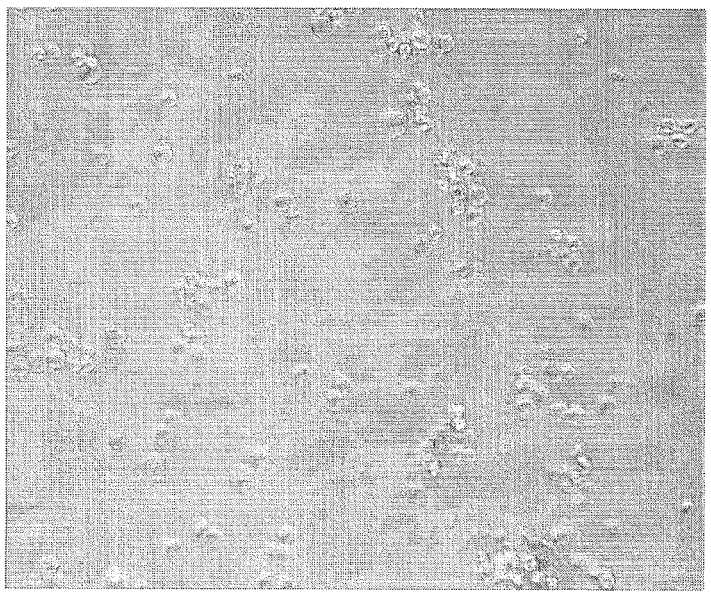
FIG. 31 is a microphotograph of GBM cancer cells after treatment with a formulation comprising a plurality of therapeutic agents.

The results are graphically shown in FIG. 30. FIG. 31 is a micrograph of GBM multicellular tumor spheroid (MTS) cells treated with carmustine, curcumin and extract sample 13 (fern) as disclosed above.

The combination of carmustine and curcumin was the most effective two agent combination in killing GBM multicellular tumor spheroid cells. Adding extract sample 13 to the combination of carmustine and curcumin surprisingly increased cytotoxic activity in GBM multicellular tumor spheroid cells by about 50 percent.

Combinations of Plant Extracts with Additional Therapeutic Agents as a Therapeutic Treatment of Metastatic Colon Cancer.

The standard chemotherapeutic drugs recommended to treat metastatic colon cancer are 5-Fluorouracil and Gemcitabine. The standard chemotherapeutic protocol is use of 5-fluorouracil at 2.5 μM for 5 days or Gemcitabine at 5 μM for 5 days for in vitro culture assays.

Single agent treatment of metastatic colon cancer.

Figure 32:
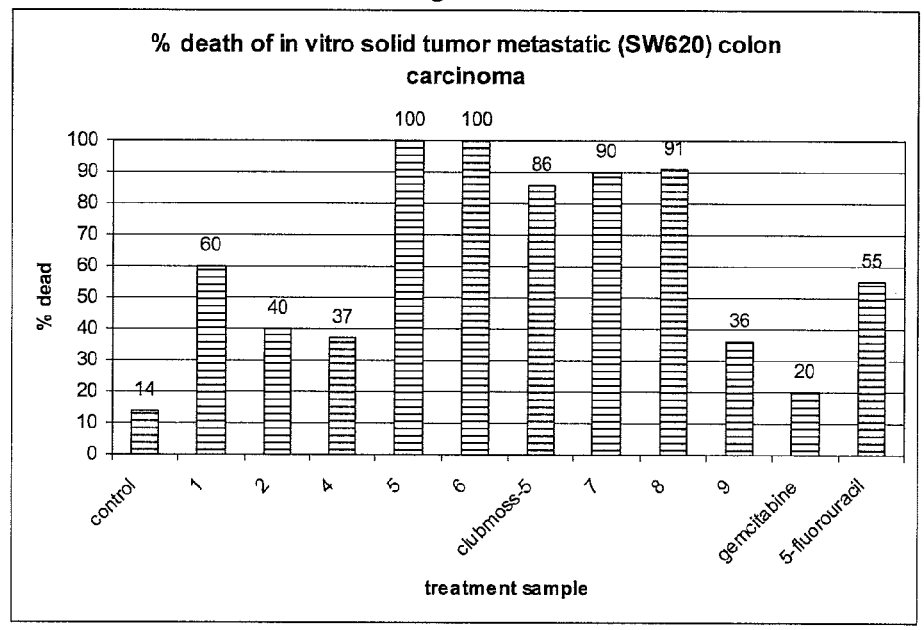
FIG. 32 is a graph of colon cancer cell death after exposure to a therapeutic agent.

Metastatic MTS colon cancer (SW620) were treated for 24 hours with extract samples 1 (moss), 2 (moss), 4 (moss), 6 (moss), 5 (moss), 7 (fern), 8 (fern), 9 (moss), all at 50 mg/mL, and for 5 days with the standard chemotherapeutics 5-fluorouracil at 2.5 μM and Gemcitabine at 5 μM. Results are shown below and in FIG. 32.

TABLE 18

| treatment sample | % live cells | % dead cells |
| --- | --- | --- |
| no treatment (control) | 86 | 14 |
| 1, moss | 40 | 60 |
| 2, moss | 60 | 40 |
| 4, moss | 63 | 37 |
| 5, moss | 0 | 100 |
| 6, moss | 0 | 100 |
| 7, fern | 10 | 90 |
| 8, fern | 9 | 91 |
| 9, moss | 64 | 36 |
| Gemcitabine | 80 | 20 |
| 5-fluorouracil | 45 | 55 |

Most of the extract samples were more effective at killing solid metastatic colon cancer MTS cells after 24 hours then the standard chemotherapeutics 5-fluorouracil (at 2.5 μM) or Gemcitabine (at 5 μM) after 5 days.

Single agent treatment of metastatic colon cancer.

Figure 33:
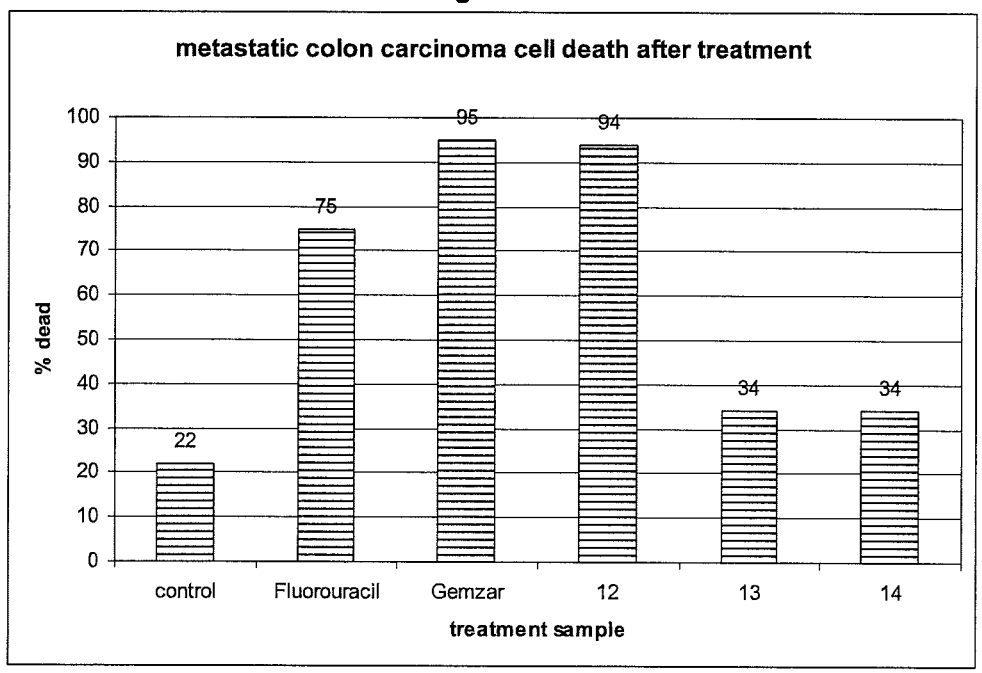
FIG. 33 is a graph of metastatic colon cancer cell death after exposure to a therapeutic agent.
Figure 34:
FIG. 34 is a microphotograph of 227 colon cancer cells after 48 hour exposure to extract sample 13, 14K pellet, 10 mg/mL dose.
Figure 35:
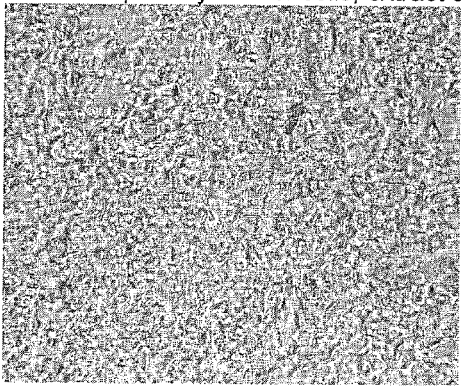
FIG. 35 is a microphotograph of 227 colon primary cancer cells after 48 hour exposure to extract sample 13, 14K supernatant.
Figure 36:
FIG. 36 is a microphotograph of NCI-H1299 lung cancer cells after 48 hour exposure to extract sample 13, filtered 14K pellet.
Figure 37:
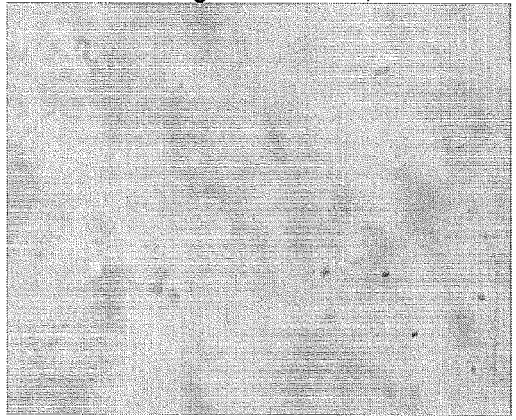
FIG. 37 is a microphotograph of NCI-H1299 lung cancer cells after 48 hour exposure to extract sample 13, 14K supernatant.
Figure 38:
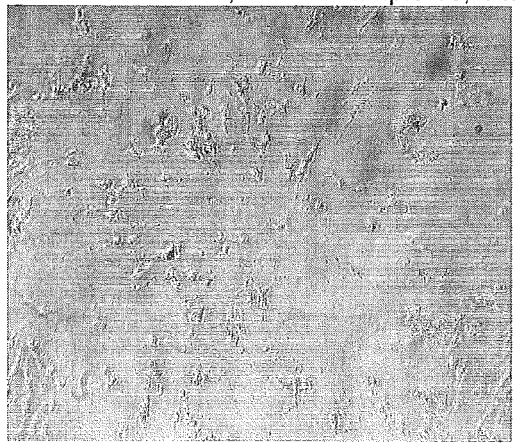
FIG. 38 is a microphotograph of GBM cancer cells after 48 hour exposure to extract sample 13, 14K pellet.
Figure 39:
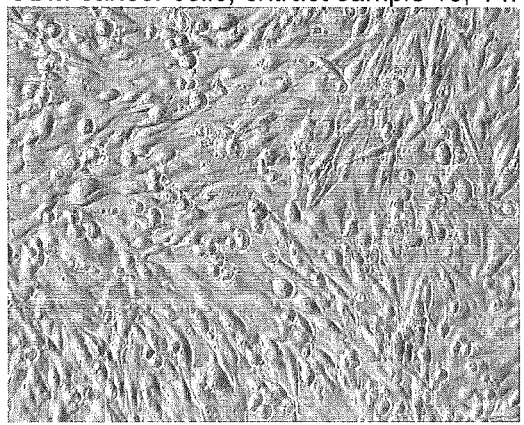
FIG. 39 is a microphotograph of GBM cancer cells after 48 hour exposure to extract sample 13, 14K supernatant.
Figure 40:
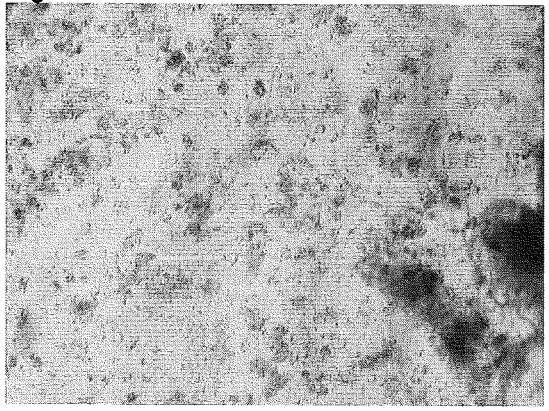
FIG. 40 is a microphotograph of GBM cancer cells after 24 hour exposure to extract sample 13, unfiltered 14K pellet, 10 mg/mL dose.
Figure 41:
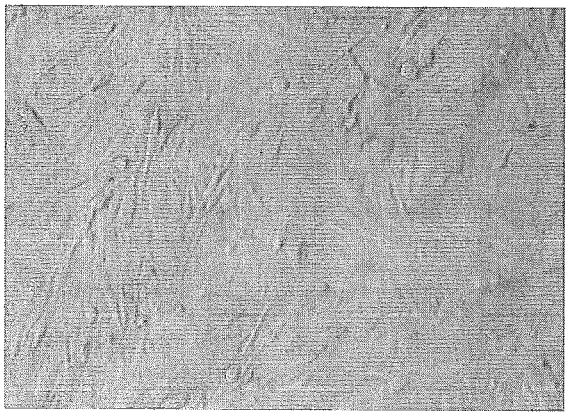
FIG. 41 is a microphotograph of GBM cancer cells after 24 hour exposure to extract sample 13, 14K supernatant, 10 mg/mL dose.
Figure 42:
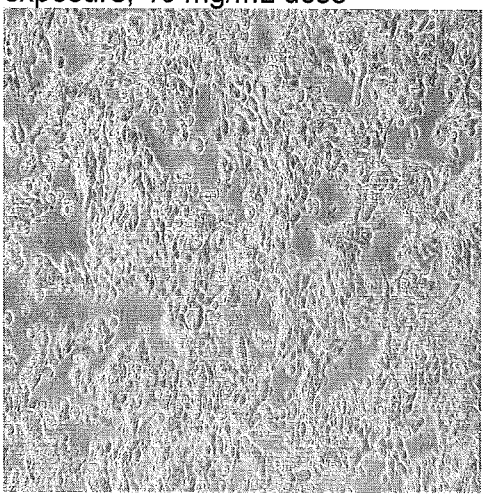
FIG. 42 is a microphotograph of 227 primary colon cancer cells after 24 hour exposure to extract sample 13, membrane filtered, 10 mg/mL dose.
Figure 43:
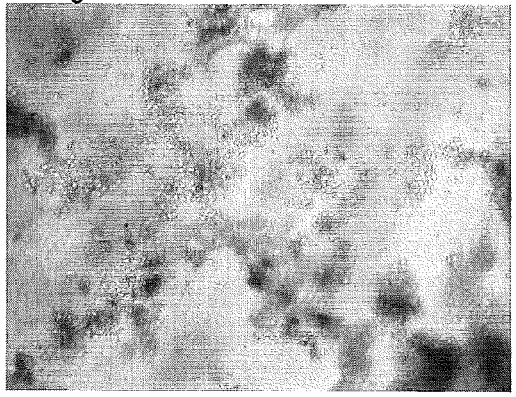
FIG. 43 is a microphotograph of primary colon cancer cells after 24 hour exposure to extract sample 13, unfiltered 14K pellet, 10 mg/mL dose.
Figure 44:
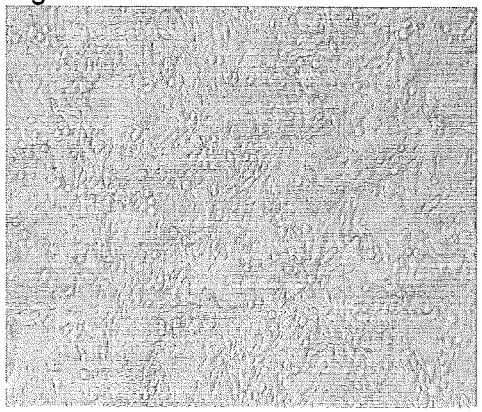
FIG. 44 is a microphotograph of primary colon cancer cells after 24 hour exposure to extract sample 13, 14K supernatant, 10 mg/mL dose.
Figure 45:
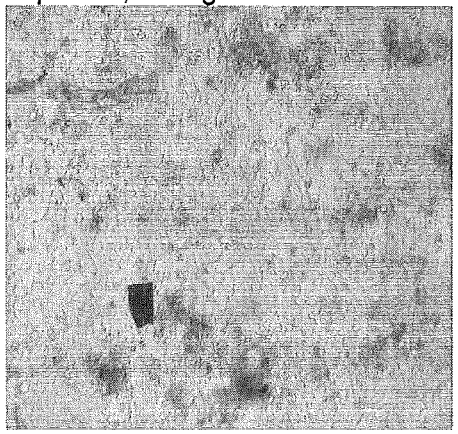
FIG. 45 is a microphotograph of primary colon cancer cells after 24 hour exposure to extract sample 13, unfractionated extract, 10 mg/mL dose.
Figure 46:
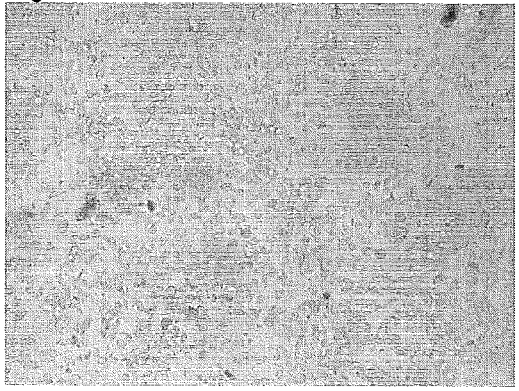
FIG. 46 is a microphotograph of 227 colon cancer cells after 48 hour exposure to extract sample 13, membrane filtered, 10 mg/mL dose.
Figure 47:
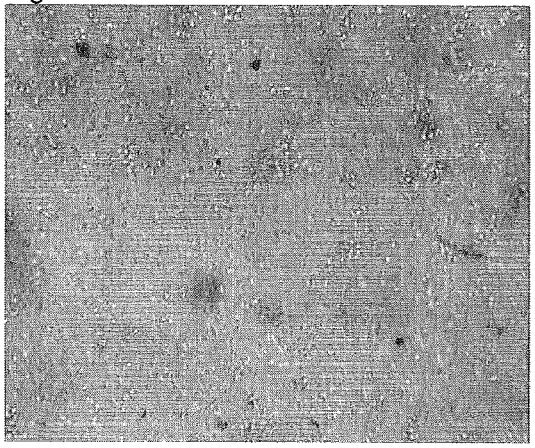
FIG. 47 is a microphotograph of 227 primary colon cancer cells after 24 hour exposure to extract sample 13, filtered pellet, 10 mg/mL dose.
Figure 48:
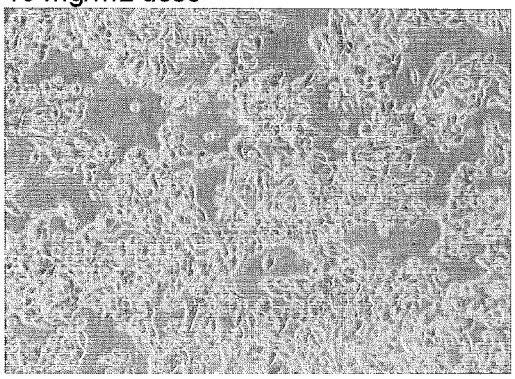
FIG. 48 is a microphotograph of 227 primary colon cancer cells after 24 hour exposure to extract sample 13, 14K supernatant, 10 mg/mL dose.
Figure 49:
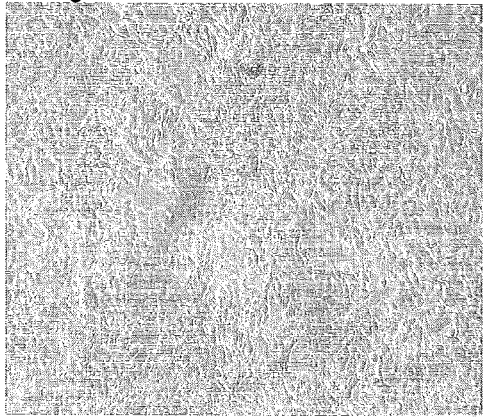
FIG. 49 is a microphotograph of 227 primary colon cancer cells after 24 hour exposure to extract sample 13, unfiltered extract, 10 mg/mL dose.
Figure 50:
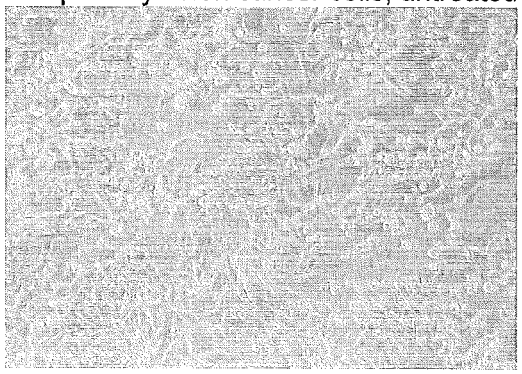
FIG. 50 is a microphotograph of 227 primary colon cancer cells, untreated control.
Figure 51:
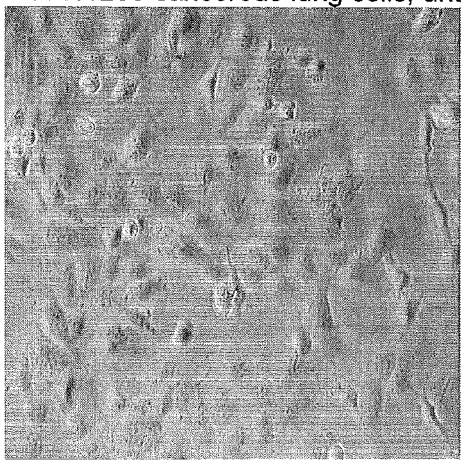
FIG. 51 is a microphotograph of NCI-H1299 cancerous lung cells, untreated control.
Figure 52:
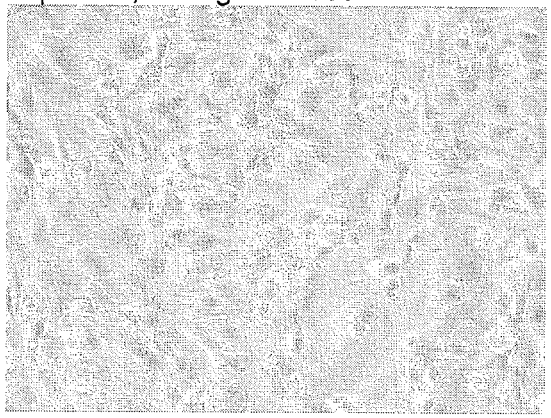
FIG. 52 is a microphotograph of NCI-H1299 cancerous lung cells after 24 hour exposure to extract sample 13, membrane filtered, 10 mg/mL dose.
Figure 53:
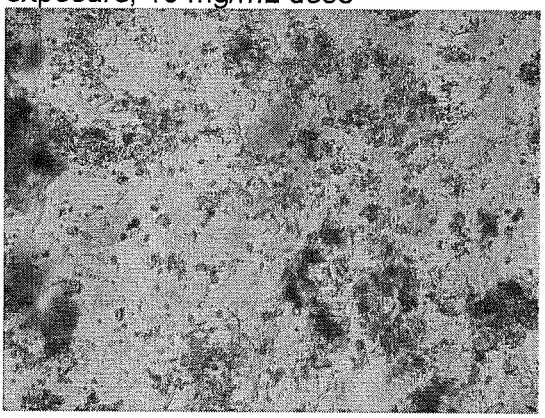
FIG. 53 is a microphotograph of NCI-H1299 cancerous lung cells after 24 hour exposure to extract sample 13, pellet (unfiltered), 10 mg/mL dose.
Figure 54:
FIG. 54 is a microphotograph of NCI-H1299 cancerous lung cells after 24 hour exposure to extract sample 13, 14K supernatant, 10 mg/mL dose.
Figure 55:
FIG. 55 is a microphotograph of NCI-H1299 cancerous lung cells after 24 hour exposure to extract sample 13, filtered pellet, 10 mg/mL dose.
Figure 56:
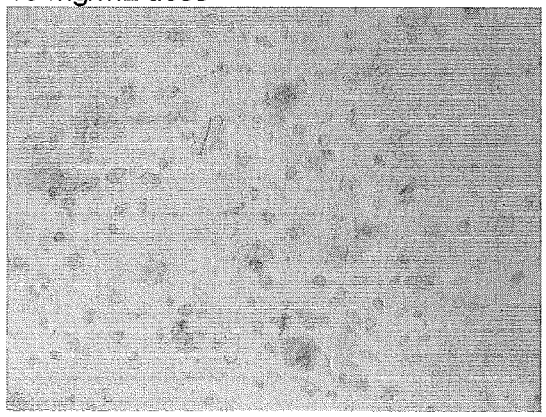
FIG. 56 is a microphotograph of NCI-H1299 cancerous lung cells after 48 hour exposure to extract sample 13, filtered pellet, 10 mg/mL dose.
Figure 57:
FIG. 57 is a microphotograph of NCI-H1299 cancerous lung cells after 48 hour exposure to extract sample 13, membrane filtered, 10 mg/mL dose.
Figure 58:
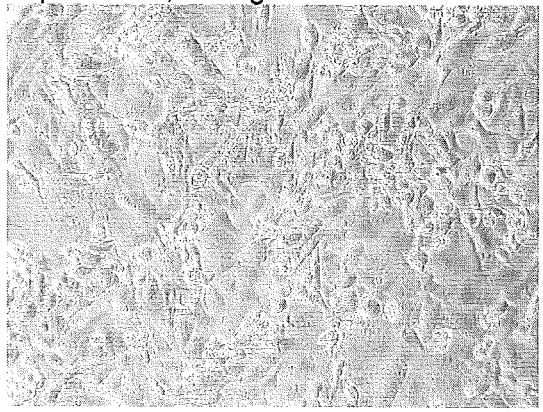
FIG. 58 is a microphotograph of NCI-H1299 cancerous lung cells after 24 hour exposure to extract sample 13, 14K supernatant, 10 mg/mL dose.
Figure 59:
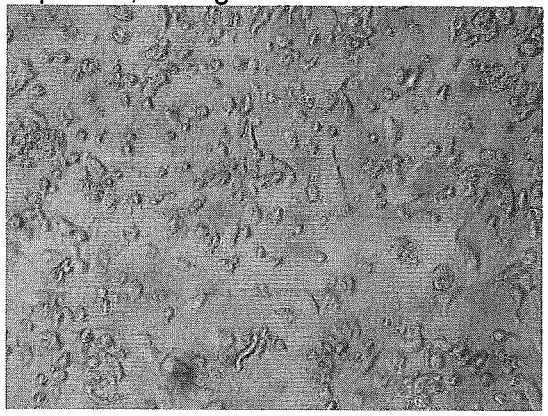
FIG. 59 is a microphotograph of NCI-H1299 cancerous lung cells after 48 hour exposure to extract sample 13, 14K supernatant, 10 mg/mL dose.
Figure 60:
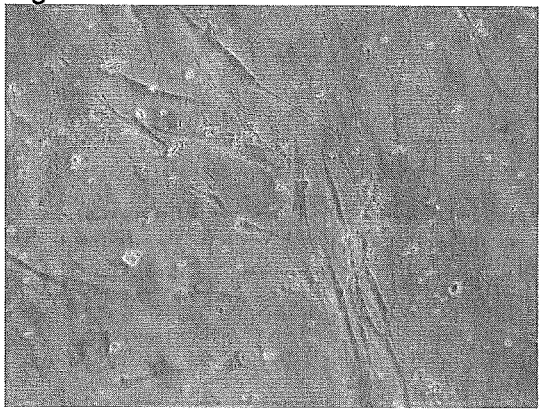
FIG. 60 is a microphotograph of WI38 normal lung cells after 24 hour exposure to extract sample 13, membrane filtered, 10 mg/mL dose.
Figure 61:
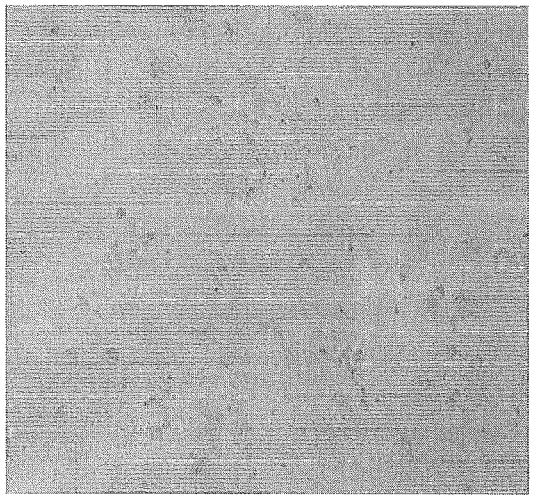
FIG. 61 is a microphotograph of WI38 normal lung cells after 48 hour exposure to extract sample 13, filtered pellet, 10 mg/mL dose.
Figure 62:
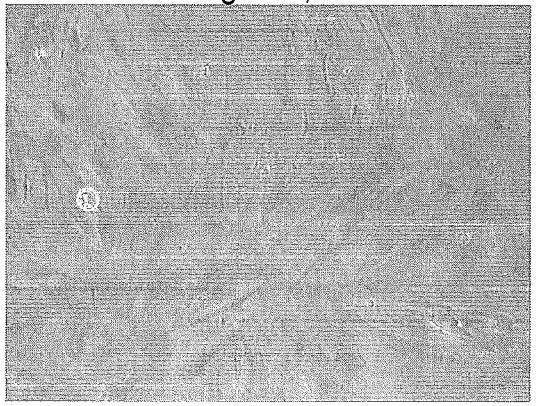
FIG. 62 is a microphotograph of WI38 normal lung cells, untreated control.
Figure 63:
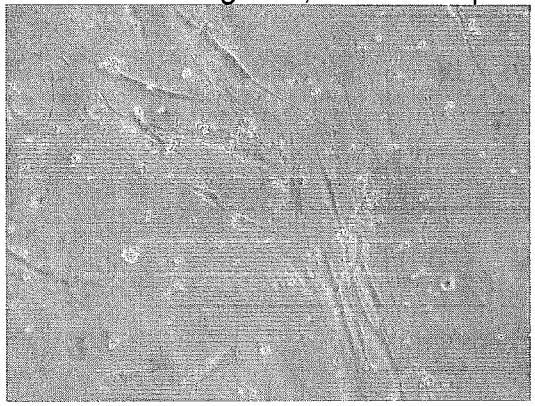
FIG. 63 is a microphotograph of WI38 normal lung cells after 24 hour exposure to extract sample 13, filtered, 10 mg/mL dose.

Metastatic colon cancer (SW620) MTS cells were treated for 24 hours with extract samples 12 (moss), 13 (fern), 14 (lichen), all at 50 mg/mL, and for 5 days with the standard chemotherapeutics 5-fluorouracil at 2.5 μM and Gemcitabine at 5 μM. Results are shown below and in FIG. 33.

TABLE 19

| treatment sample | % live cells | % dead cells |
| --- | --- | --- |
| no treatment (control) | 88 | 22 |
| 12, moss | 6 | 94 |
| 13, fern | 66 | 34 |
| 14, lichen | 66 | 34 |
| Gemcitabine | 5 | 95 |
| 5-fluorouracil | 25 | 75 |

Extract Sample Fractionation Study

Extract samples from primitive plant 13 (fern) were prepared according to the previously disclosed procedure. The prepared extract samples were further evaluated in a fractionation study in which the extract sample was separately modified by filtration and centrifugation.

Filtration

The extract sample homogenate was poured into a 20 cc syringe barrel, the barrel was attached to 0.22 micron filter (mixed cellulose ester Whatman Syrfil-MF) and then a syringe plunger was used to force the liquid contents through the pores of the filter membrane to separate the liquid portion of the plant homogenate from the solid plant material. The liquid filtrate was then added to the cells in culture using a micropipettor at a concentration of 10 mg/mL. The cell types assayed included Glioblastoma multiforme, non-small cell lung carcinoma, and primary colon carcinoma all cultured as monolayers. The tumor cells were exposed to the filtrate for periods of time ranging from 24 hrs to 48 hrs at 37° C. and then examined by microscopy to assess visible effects of the filtered extract in inducing cancer cell death on the cultured cells and then photographed.

Centrifugation

Fractionation of the extract sample homogenate by differential centrifugation was accomplished by placing the homogenate in 2.0 mL microcentrifuge tubes and placing the tubes in a microcentrifuge. The extract sample was then centrifuged at a speed of 14,000 rpm for a period of 30 minutes at room temperature. The tubes were removed from the microcentrifuge and the liquid supernatant was carefully removed with a Pasteur pipette and placed in a separate tube, effectively separating the liquid portion of the extract sample homogenate from the solid portion of the extract sample homogenate. The solid portion formed a pellet at the bottom of the tube due to its greater density during centrifugation. The liquid supernatant and the pellet portions were then used separately as therapeutic agents to treat cancer cells at concentrations of approximately 10 mg/mL. The liquid supernatant was added to the cultured cells using a micropipettor.

The pellet portion of the extract sample homogenate was treated further before it was added to the cells in one of two ways:

1) The extract sample pellet was resuspended in 100 microL of phosphate buffered saline (PBS), pipetted up and down using a micropipettor and then added directly to the cells using a micropipettor whose tip was cut off slightly to produce a greater diameter to accommodate the solid material.

2) the extract sample pellet was resuspended in 100 microL of phosphate buffered saline (PBS), pipetted up and down using a micropipettor and then filtered through a 0.22 micron filter (Whatman Syrfil-MF methyl cellulose ester) by placing the contents in the barrel of a 1 cc syringe and using the plunger to force the resuspended plant pellet material through the pores of the filter. The liquid filtrate was then added to the cells using a micropipettor at a final concentration of approximately 10 mg/mL. The cell types assayed included Glioblastoma multiforme, non-small cell lung carcinoma, and primary and metastatic colon carcinoma all cultured as monolayers. The tumor cells were exposed to the filtrate for periods of time ranging from 24 hrs to 48 hrs at 37° C. and then examined by microscopy to assess visible effects of the filtered extract on the cultured cells and then photographed.

The results of extract sample fractionation were assessed by photomicroscopy imaging of the cultured monolayer cells following defined periods of treatment with the fractionated plant material. These results are illustrated in FIGS. 34 to 63. These figures illustrate cytotoxic effects from the fractionated extract sample, including cell detachment from the substrate to produce floating cells as individual cells or as clumped aggregates; rounding up of the cell surface/membrane; and low proliferative activity indicated by the absence of confluent growth and minimal numbers of cells on the culture dishes. These qualitative assessments provide a reliable indication of the general presence of cytotoxicity in the homogenate fractions assessed in this study.

The results of this study showed that different homogenate components produced different cytotoxic effects when used to treat the cultured tumor cells under comparable assay conditions. The liquid filtrate prepared by homogenate filtration in the absence of centrifugation produced little cytotoxic effect. The cells remained attached to the substrate and were observed to proliferate in a manner comparable to untreated control cultures of tumor cells. Likewise, the liquid supernatant produced by centrifugation of the plant homogenate extract was observed to produce minimal cytotoxic effects. In contrast, the 14K unfiltered pellet produced by centrifugation of the plant homogenate produced maximal cytotoxic effects in the cultured tumor cells that was associated with substrate detachment, rounding up of the tumor cells and low cell numbers compared to the untreated cultures or cultures treated with liquid fractions of the homogenate. The filtrate produced by passing the resuspended pellet through a 0.22 micron filter also produced significantly greater levels of cytotoxicity in the cultured cells than did the liquid portion of the homogenate. Taken together, these observations indicated that the major portion of the cytotoxic activity of the plant homogenate is retained in the solid plant matter fraction following homogenate preparation rather than representing a diffusible small molecule component present in the liquid medium.

The data illustrates the major biological effects of the primitive plant extract samples as they relate to therapeutic and/or preventive anti-cancer properties. These effects include potent induction of cell death responses in both monolayer and solid tumor cultures for all assessed human malignancies. The observed responses are based on cell viability counts and survival assay data. Quantitative differences in activity were observed in extracts prepared from different plant species; however, all extracts tested showed evidence of significant therapeutic activity. Optimal dosing range for the example extracts was determined to be 25-50 mg/ml. Time course assessment showed rapid cell death effects with cytotoxic responses observed within 12 to 24 hours treatment.

The anti-cancer effects of the extract samples are effective against a broad spectrum of human malignancies of varying tissue and cellular origins, encompassing most common types of human cancer.

While there is no in vivo data, the results for the in vitro three dimensional solid tumor cultures are indicative of the extract performance in vivo. Based on the in vitro three dimensional solid tumor data the extracts are believed to possess significant in vivo therapeutic activity for killing cancer cells.

The data illustrate minimal cytotoxicity to normal human tissue under dosing concentrations and treatment times similar to those used to assess anti-cancer activity. The data are based on cell viability assessments and on cell-to substrate attachment parameters.

The data illustrates preventive effects on solid tumor formation in vitro. The data are based on survival assays and the absence of formation of viable solid tumor aggregates in vitro.

The anti-cancer effects of primitive plant extracts appear to involve disruption of cytoskeletal network of cancer cells in both treated monolayer cultures and in solid tumors. This assessment is based on fluorescent confocal microscopy of cytoskeletal network structural organization in untreated versus treated tumor cells (see FIGS. 24 to 29).

This disclosure demonstrates that diverse groups of primitive plants, including many or most species of primitive mosses, ferns and lichens, have novel and potent anti-cancer properties over a diverse group of unrelated human cancers, suggesting a common therapeutic target important to abnormal tumor physiology. These plants can be processed to prepare an extract possessing anti-cancer properties having significant potential for both the prevention of cancer as well as clinical treatment of patients with cancer. The primitive plant extracts can be used to prevent or treat many cancers, either alone or in combination with other therapeutic agents. The disparate levels of cytotoxicity observed in tumor cells versus normal cells in culture suggest that primitive plant extracts display the potential for a relatively high therapeutic index.

While preferred embodiments have been set forth for purposes of illustration, the foregoing description should not be deemed a limitation of the disclosure herein. Accordingly, various modifications, adaptations and alternatives may occur to one skilled in the art without departing from the spirit and scope of the present disclosure.

What is claimed:

1. A method of treating a cancer selected from the group consisting of colon cancer, glioblastoma multiforme, and non-small cell lung cancer in a human in need thereof consisting essentially of:
administering a therapeutically effective amount of a capsule or tablet consisting essentially of a plant extract selected from the group consisting of sphagnum moss extract, maidenhair fern extract, tree fern extract, club moss extract, Christmas fern extract and lichen extract and a therapeutic agent selected from the group consisting of carmustine, berberine, curcumin, abscistic acid, 5-fluorouracil, gemcitabine, and caffeic acid phenyl ester to said human in need thereof to effectively treat said cancer selected from the group consisting of colon cancer, glioblastoma multiforme, and non-small cell lung cancer in said human.

2. A method of treating a cancer selected from the group consisting of colon cancer, glioblastoma multiforme, and non-small cell lung cancer in a human in need thereof consisting essentially of:

administering a therapeutically effective amount of a slow release microcarrier consisting essentially of a plant extract selected from the group consisting of sphagnum moss extract, maidenhair fern extract, tree fern extract, club moss extract, Christmas fern extract and lichen extract and a therapeutic agent selected from the group consisting of carmustine, berberine, curcumin, abscistic acid, 5-fluorouracil, gemcitabine, and caffeic acid phenyl ester to said human in need thereof to effectively treat said cancer selected from the group consisting of colon cancer, glioblastoma multiforme, and non-small cell lung cancer in said human.

* * * * *

UNITED STATES PATENT AND TRADEMARK OFFICE
CERTIFICATE OF CORRECTION

| | | |
|---|---|---|
| PATENT NO. | : 8,945,635 B2 | |
| APPLICATION NO. | : 13/964154 | |
| DATED | : February 3, 2015 | |
| INVENTOR(S) | : Sarah Crawford | |

It is certified that error appears in the above-identified patent and that said Letters Patent is hereby corrected as shown below:

On the Title Page

Column 2, cover sheet, Abstract, line 5, "...prevent growth of cancer cells and teat cancer." should be -- ...prevent growth of cancer cells and treat cancer. --

In the Drawings

Fig. 9 "...exttract..." should be -- ...extract... --

In the Specification

Column 7, lines 27-28, "Six millileters of ... was added to each vial." should be -- Six millileters of ... were added to each vial."

Column 7, lines 29-30, "All but the cap portion of each vial was ... until the cells are thawed." should be -- All but the cap portion of each vial was ... until the cells were thawed. --

Column 7, line 31, "The cells are ... and the flasks were then..." should be -- The cells were ... and the flasks were then... --

Column 8, line 66, "1% Argarose gel was..." should be -- 1% Agarose gel was... --

Column 10, line 4, "6 drops of PBS is added to each well." should be -- 6 drops of PBS are added to each well. --

Column 10, line 7, "6 drops of trypsin is added to each well." should be -- 6 drops of trypsin are added to each well. --

Signed and Sealed this
Twenty-fifth Day of August, 2015

Michelle K. Lee
*Director of the United States Patent and Trademark Office*

CERTIFICATE OF CORRECTION (continued)
U.S. Pat. No. 8,945,635 B2

Column 10, line 67, "...with a small a mount of..." should be -- ...with a small amount of... --

Column 12, line 16, "The most practical forms of storage is:" should be -- The most practical form of storage is: --

Column 13, line 17, "...(in the dark and were then allowed..." should be -- ...in the dark and were then allowed... --

Column 18, line 5, "...Table I..." should be -- ...Table 1... --

Column 20, lines 35-36, "FIG. 15 shows a glioblastoma ... cells cultured as monolayers." should be -- FIG. 15 shows glioblastoma ... cells cultured as monolayers." --

Column 25, line 45, "Metasttic MTS colon cancer (SW620) were treated for..." should be -- Metastic MTS colon cancer (SW620) cells were treated for... --

Column 25, lines 66-67, "...samples were more effective at killing solid after 24 hours then..." should be -- ... samples were more effective at killing solid ... after 24 hours than... --

Column 28, line 14, "...based on cell viability assessments and on cell-to substrate attachment parameters." should be -- ...based on cell viability assessments and on cell-to-substrate attachment parameters. --